(12) United States Patent
de Beaubien et al.

(10) Patent No.: US 11,877,859 B2
(45) Date of Patent: Jan. 23, 2024

(54) SOFT TISSUE TENSION GUIDED BONE RESECTION INSTRUMENTS AND METHODS

(71) Applicant: MicroPort Orthopedics Inc., Arlington, TN (US)

(72) Inventors: Brian C. de Beaubien, Fenton, MI (US); Brian R. Harris, Jr., Cordova, TN (US)

(73) Assignee: MicroPort Orthopedics Holdings Inc., Arlington, TN (US)

(*) Notice: Subject to any disclaimer, the term of this patent is extended or adjusted under 35 U.S.C. 154(b) by 273 days.

(21) Appl. No.: 17/491,617

(22) Filed: Oct. 1, 2021

(65) Prior Publication Data

US 2022/0015690 A1 Jan. 20, 2022

Related U.S. Application Data

(63) Continuation of application No. 16/423,006, filed on May 25, 2019, now Pat. No. 11,166,663.
(Continued)

(51) Int. Cl.
*A61B 17/15* (2006.01)
*A61B 17/02* (2006.01)
(Continued)

(52) U.S. Cl.
CPC .......... *A61B 5/4533* (2013.01); *A61B 5/4585* (2013.01); *A61B 17/1764* (2013.01);
(Continued)

(58) Field of Classification Search
CPC ... A61B 5/4533; A61B 5/4585; A61B 17/155; A61B 2017/0268
See application file for complete search history.

(56) References Cited

U.S. PATENT DOCUMENTS 5,578,039 A 11/1996 Vendrely et al.
6,013,081 A 1/2000 Burkinshaw et al.
(Continued)

FOREIGN PATENT DOCUMENTS

WO WO2013057514 A1 4/2013

OTHER PUBLICATIONS

Wright Medical Technology, Inc. Evolution Medial-Pivot Knee System Surgical Technique, Distal Cut First, Jul. 7, 2013, pp. 1-48, Arlington, TN, USA.

*Primary Examiner* — David W Bates
(74) *Attorney, Agent, or Firm* — Robert J. Hornung

(57) ABSTRACT

A device for preparing a femur of a patient for receipt of a knee implant in both extension and flexion relative to a resected tibia plateau based on applying tension to medial and lateral collateral ligaments of said patient, comprising a tibial baseplate, a tensioner, the tensioner comprising a tensioner body having a tensioner portion, the tensioner portion affixed to the tibial baseplate, and an expander arm comprising an elongated body portion, a superior side of the elongated body portion having a spiked tip adjacent a posterior end thereof. The spiked tip interacts with an intracondylar notch under tension. The expander arm is operatively connected to the tensioner body via the tensioner portion, the tensioner portion configured for use in selectively raising and lowering the expander arm relative to the tibial baseplate to apply tension to the medial and lateral collateral ligaments in extension or flexion.

20 Claims, 17 Drawing Sheets

Related U.S. Application Data

(60) Provisional application No. 62/676,704, filed on May 25, 2018.

(51) Int. Cl.
  *A61B 5/00* (2006.01)
  *A61B 17/17* (2006.01)
  *A61F 2/46* (2006.01)
  *A61F 2/38* (2006.01)

(52) U.S. Cl.
  CPC ............ *A61F 2/461* (2013.01); *A61B 17/155* (2013.01); *A61B 2017/0268* (2013.01); *A61F 2/389* (2013.01); *A61F 2/3859* (2013.01); *A61F 2/3886* (2013.01)

(56) References Cited

U.S. PATENT DOCUMENTS

| | | |
|---|---|---|
| 6,059,788 A | 5/2000 | Katz |
| 6,458,135 B1 | 10/2002 | Harwin et al. |
| 7,374,563 B2 | 5/2008 | Roger et al. |
| 7,686,812 B2 | 3/2010 | Axelson, Jr. et al. |
| 7,794,467 B2 | 9/2010 | McGinley et al. |
| 8,425,524 B2 | 4/2013 | Aker et al. |
| 8,444,651 B2 | 5/2013 | Kunz et al. |
| 8,591,516 B2 | 11/2013 | Metzger et al. |
| 8,672,945 B2 | 3/2014 | Lavallee et al. |
| 8,734,453 B2 | 5/2014 | Tuttle et al. |
| 8,740,910 B2 | 6/2014 | McMillen et al. |
| 8,974,459 B1 | 3/2015 | Axelson, Jr. et al. |
| 8,998,908 B2 * | 4/2015 | Tuttle .................... A61F 2/4657 606/87 |
| 9,113,957 B2 | 8/2015 | Axelson, Jr. et al. |
| 9,855,057 B2 | 1/2018 | Axelson, Jr. et al. |
| 10,130,375 B2 | 11/2018 | Yager et al. |
| 2007/0173851 A1 | 7/2007 | McMillen et al. |
| 2008/0161815 A1 | 7/2008 | Schoenefeld et al. |
| 2010/0121334 A1 | 5/2010 | Couture et al. |
| 2010/0217338 A1 | 8/2010 | Carroll et al. |
| 2010/0268240 A1 | 10/2010 | McGinley et al. |
| 2016/0106409 A1 * | 4/2016 | Moholkar ............ A61B 5/4851 606/90 |
| 2018/0177612 A1 * | 6/2018 | Trabish ................ A61B 5/4528 |
| 2019/0046215 A1 | 2/2019 | Zimmer |
| 2019/0336141 A1 * | 11/2019 | Erickson ............ A61B 17/1675 |
| 2019/0388158 A1 * | 12/2019 | Mahfouz ............ A61F 2/3868 |

* cited by examiner

SOFT TISSUE TENSION GUIDED BONE RESECTION INSTRUMENTS AND METHODS

CROSS REFERENCE TO RELATED APPLICATIONS

This application claims benefit of U.S. Nonprovisional patent application Ser. No. 16/423,006, filed on May 25, 2019, which in turn claims the benefit of U.S. Provisional Application No. 62/676,704, filed on May 25, 2018. The disclosures of these related applications are hereby incorporated into this disclosure in their entirety.

FIELD OF THE INVENTION

The present invention relates to knee arthroplasty, and more particularly to instruments and methods using ligament tension for accurate placement of knee implant components.

BACKGROUND OF THE INVENTION

Standard total knee arthroplasty ("TKA") techniques based on measured resections result in somewhat arbitrary bone cuts. This often necessitates subsequent soft tissue releases in order to achieve proper ligament balancing and a stable well-functioning joint.

Most TKA systems focus on adapting the flexion gap (through rotation of the femur), to match the extension gap that was previously created. The goal is to achieve mechanical alignment of the limb through accurate coronal varus/valgus positioning of implants, resulting in a plumb line running from the hip center, through the knee center, and to the ankle center. In an industry standard scenario, a "femur first" approach is taken. The distal femoral cut (valgus angle) is made first, based on a desired angle. The desired angle is determined through an intramedullary alignment guide, a computerized navigation system, or a patient specific prefabricated cutting guide. Subsequently, the tibial cut is made. This is done with either extra-medullary or intramedullary alignment, navigation, or a prefabricated cutting guide. The resultant extension gap that is created may not be rectangular, in which case it has to be transformed into a rectangular space, which is typically done by performing soft tissue balancing procedures on the MCL (varus aligned knee), but sometimes on the LCL and other lateral structures (valgus aligned knee).

It is important to note that in the foregoing procedures, the femoral and tibial cuts are determined independently, and then the soft tissue procedure is performed in order to reconcile the non-parallel bone cuts and make them parallel. The new bone cut surfaces are frequently slightly different than the patient's natural anatomic state. The surgeon is essentially putting new implant surfaces on the bone cuts and then adjusting the ligaments to accommodate the position of the implants.

In the conventional extension gap process described above, a tensioner typically is not used to make the cuts. However, a tensioner may be used after the femoral and tibial cuts have been made in order to facilitate the soft tissue balancing/ligament releasing portion of the extension gap balancing process.

Once the above mentioned extension gap has been determined, the process moves on to the flexion gap. A tensioner may be utilized at this point. However, no further soft tissue balancing is typically done after this point because it will also affect the previous extension gap. The tensioner utilizes the existing soft tissue balance, and effectively guides the posterior femoral cut, making the posterior femoral condylar cuts parallel to the tibial cut surface by guiding/setting the femoral rotation. This typically achieves a rectangular flexion gap.

The amount of bone resected off of the posterior femoral condyles will ultimately determine the size of the flexion gap. The goal is to have the flexion gap equal the extension gap. The amount of bone resected is technique and system specific; for instance, the amount depends on whether a system is anterior or posterior referencing.

In most existing systems, the femoral and tibial surfaces are cut independently and are not linked together. The exception to this would be the last mentioned description of the femoral rotation being linked directly to the tibial cut via a tensioner in the flexion gap preparation.

There is a need for instruments and techniques that rely on the natural collateral ligament length and the ability to tension these ligaments to position bone cuts in a way that lessens the need for subsequent soft tissue balancing in order to achieve rectangular as well as equal flexion and extension gaps.

OBJECTS AND SUMMARY OF THE INVENTION

It is an object of the invention to provide a tensioner device configured for use in setting both extension and flexion gaps in knee procedures.

It is another object of the invention to use the native length and tension of the MCL to link the tibial and femoral bone cuts together in both extension and flexion gap preparation to position knee implants for optimal function.

It is yet another object of the invention to provide methods of using a tensioner device to set extension and flexion gaps based on ligament tension.

The foregoing objectives are achieved by providing surgical instruments and techniques having the features described herein.

The invention includes a device for preparing a femur of a patient for receipt of a knee implant in both extension and flexion relative to a resected tibia plateau based on applying tension to medial and lateral collateral ligaments of said patient, comprising a tibial baseplate configured to rest on said resected tibial plateau, a tensioner, the tensioner comprising a tensioner body having a tensioner portion, the tensioner portion affixed anteriorly to the tibial baseplate, an expander arm comprising an elongated body portion, a superior side of the elongated body portion having a spiked tip adjacent a posterior end thereof, the spiked tip positioned to selectively interact with an intracondylar notch of the knee under tension, the expander arm operatively connected to the tensioner body via the tensioner portion, the tensioner portion configured for use in selectively raising and lowering the expander arm relative to the tibial baseplate to thereby apply tension to said medial and lateral collateral ligaments of said patient in extension or in flexion, and a resection arm assembly, the resection arm assembly configured for selective attachment to the expander arm, the resection arm assembly including a main body portion, the main body portion supporting a medial paddle, the medial paddle configured to abut against the medial condyle.

In embodiments, the expander arm is operatively connected to the tensioner portion via a rack post, the rack post having a plurality of ratchet teeth configured to engage the tensioner portion for use in selectively raising or lowering the expander arm relative to the tibial baseplate. The tensioner portion can have a drive bore extending therethrough, the drive bore operatively receiving the rack post therein.

In embodiments, the tibial baseplate is substantially planar. The tensioner portion is affixed anteriorly to the tibial baseplate via an extension portion of the tibial baseplate.

The resection arm assembly further comprises an attachment base and a main body portion slidingly mounted on the attachment base via a post, the attachment base configured to slide onto the expander arm. The main body portion is configured to selectively lock the main body portion to the post of the attachment base when said knee is in extension or in flexion, to thereby maintain a selected position of said resection arm assembly relative to said knee. The main body portion has pin bores formed therethrough for use in setting pin placement, the pin bores positioned to correspond with pin bores on associated resection guides. The pin bores can include a pair of extension bores for setting pin placement when in extension and a pair of flexion bores for setting pin placement when in flexion.

In embodiments, the attachment base has a lengthwise channel sized and configured to receive the elongated body portion of the expander arm therein. The expander arm body portion of the expander arm is provided with a pair of opposing tracks, and the lengthwise channel of the attachment base has a pair of opposing rails, the rails sized and configured to slide into the tracks from an anterior-to-posterior orientation.

The spiked tip interacting with the intercondylar notch and the medial paddle interacting with the posterior condyle are sized and configured to maintain a natural space between a leading face of the main body portion of the resection arm assembly and a resected distal condyle. A flexion spacer is configured to attach to the leading face of the main body portion and sized to fill the natural space.

An extension angle guide is selectively attachable to the resection arm assembly in extension, the extension angle guide configured for use in setting a distal femoral resection.

In embodiments, a removable stylus is provided on the main body portion of the resection arm assembly, the stylus configured for use in sizing said femur in flexion. The stylus can be a front loading stylus, for ease of attachment and detachment of the stylus.

The device is configured for use on either a left or a right knee. The resection arm assembly and the extension angle guide are provided in side specific right and left embodiments.

The invention further includes methods of using the instruments.

The foregoing and other objects, features, aspects and advantages of the invention will become more apparent from the following detailed description of the invention when considered in conjunction with the accompanying drawings.

PREFERRED EMBODIMENTS OF THE INVENTION

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

FIGS. 1-6 provide views of one embodiment of a tensioning device 100 for setting femoral resection cuts in extension and flexion. The basic concept behind the MCL-guided soft tissue tensioner 100 is the use of the native length and tension of the MCL to link the tibial and femoral bone cuts together in both extension and flexion gap preparation in order to position the implants for optimal kinematic function. In extension, this is the coronal (varus-valgus) plane for both femoral and tibial cuts. In flexion, it is the transaxial plane for the femur (femoral rotation). To a lesser extent, LCL and lateral structures can also be used in the technique.

Figure 1A:
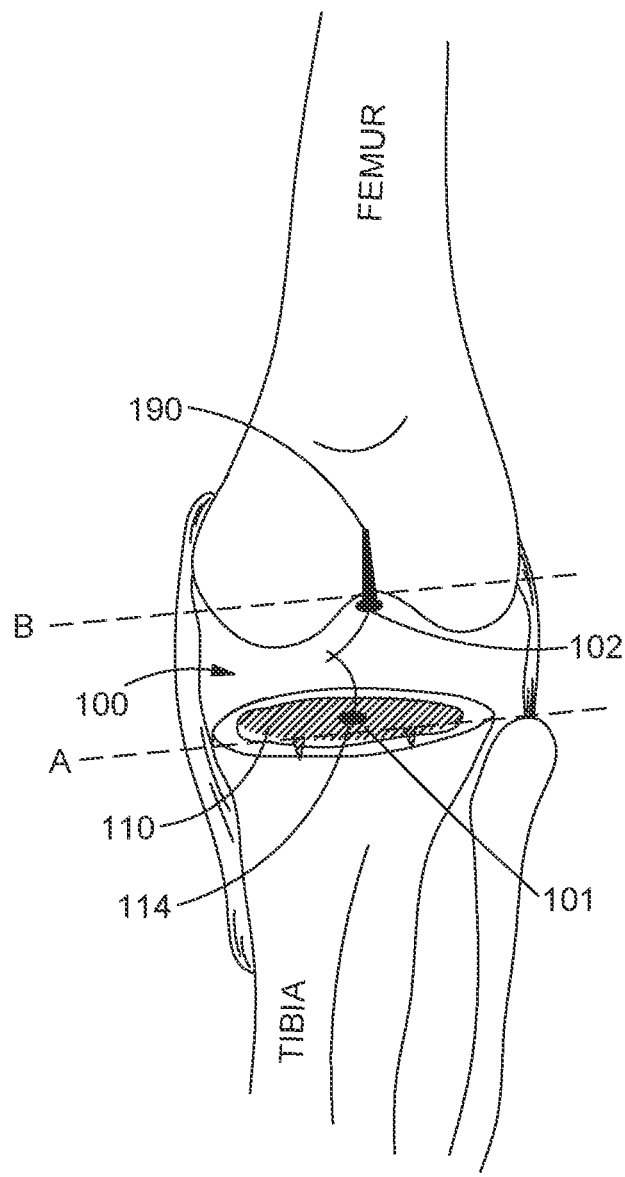
FIG. 1A is a front view of one embodiment of a tensioner assembly on a knee in extension.
Figure 1B:
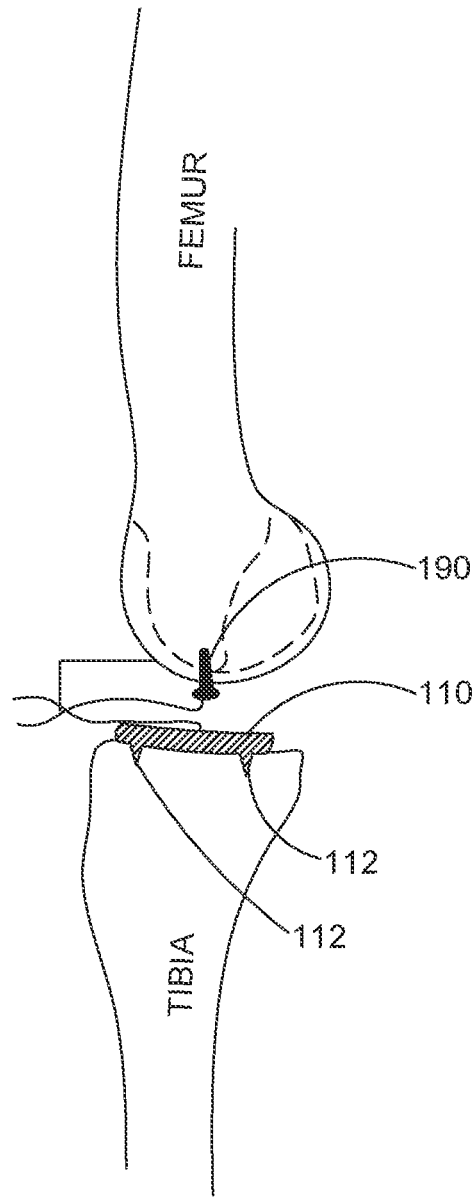
FIG. 1B is a side view of the tensioner assembly of FIG. 1A.

Unlike many conventional TKA techniques, the tensioner 100 and technique are based on a tibia cut first approach. As indicated in FIG. 1, the tibia cut is perpendicular to the long axis of the tibia T in the coronal plane, at zero degrees varus/valgus. The posterior slope matches the natural slope of the patient. As indicated in FIG. 1, the MCL guided soft tissue tensioner 100 is then positioned into the extension gap with the knee in full extension. The tensioner 100 is then expanded gently until there is slight tension on the MCL structures. As indicated in FIG. 1A, the tensioner 100 allows soft tissue (MCL/LCL and other lateral structures; IT band, popliteus tendon) to self-align the femur relative to the tibial resection surface to create parallel femoral (distal and posterior) cuts to the tibial surface, resulting in rectangular extension and flexion gaps. This effectively "links" the femoral resections to the tibial resection in both extension and flexion gaps.

In general, the balancing is accomplished through the unique design of the tensioner 100. A broad tibial baseplate 110 on a first or distal end 101 of the tensioner 100 gives the tensioner 100 a very stable foundation to anchor and push off of the cut tibia plateau surface. As shown in FIG. 1A, a thin tibial tensioner base plate 110 is applied to the cut proximal surface of the tibia. The plate 110 may have a centralized hole or hub 114 to secure the tibial/distal end 101 of the tensioner 100. The base plate of FIG. 1A may have a pair of short tibial spikes 112 on a distal side thereof for temporarily anchoring the plate 110 on the resected tibial plateau. However, the spikes 112 can be eliminated, such as in the embodiment described further below.

Figure 2:
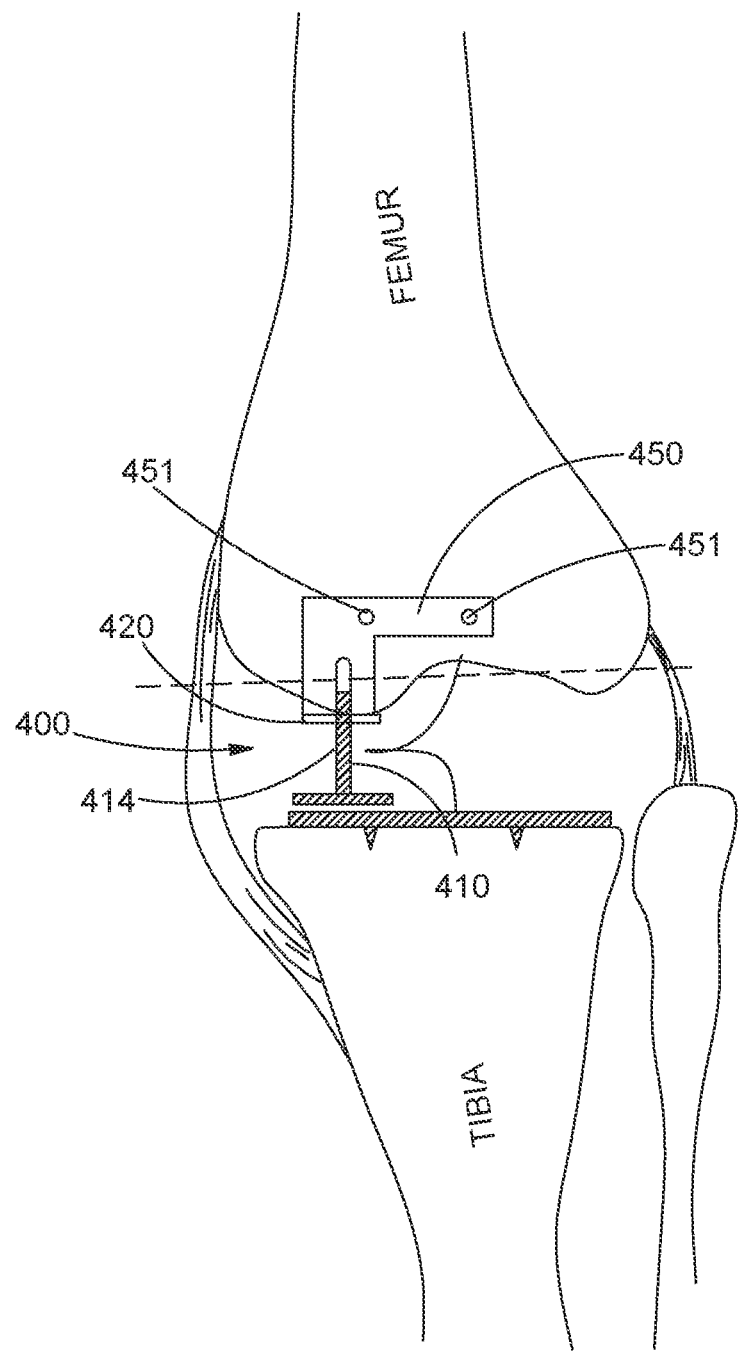
FIG. 2 is a front view of one embodiment of a slide piece/distal femoral resection measurer.

The opposite or proximal end 102 of the tensioner 100 engages the femur. In an exemplary embodiment, this occurs through interaction with a screw or spike 190. The screw or spike 190 is embedded in the distal femur just anterior to the femoral notch when the knee is in extension at 0 degrees, in the location where an intramedullary rod would be placed in a conventional IM rod TKA procedure. The femoral/proximal end 102 of the tensioner 100 is configured as a seat that pivots and rotates on the screw or spike 190 in a polyaxial relationship, with the spike 190 serving as a spherical pivot point. In extension, the location where the spike 190 engages the femur is the roof of the intercondylar notch, anterior to the flexion axis of the knee. Due to this location, as the surgeon spreads the tensioner 100 apart, it has the effect of putting the knee into slight flexion, increasing flexion as more tension is applied. This affects the pivot point in the sagittal plane as well. The expandable tensioner 100 is thus locked to the tibial plate 110 and the femoral screw 190. As the tensioner 100 expands, it pushes against the tibial surface at its distal end 101, and against the spike pivot point at a second or proximal end 102, opening up the extension gap. This causes the femur to pivot on the spike 190 in the coronal (varus/valgus) plane when the knee is in extension, and in the axial plane when the knee is in flexion. This action occurs in direct response to the collateral ligaments acting as checkreins on the femur. Tension is applied until the MCL acts as a check rein. The lateral collateral ligament will also tighten, since the tensioner is in the midline. As shown in FIG. 2, this results in the femur being held in position by the tensioner 100 and the collateral ligaments. Any ostophytes that are limiting placement or movement are removed so as not to affect the collateral ligament tension, especially of the MCL. More attention is paid to the tension on the MCL than on the LCL. As in the natural knee, the medial side is under more tension than the lateral side.

As shown in FIG. 2, the slide piece/distal femoral resection measurer 400 is now inserted into the medial joint space. The slide piece 400 is hooked onto the tensioner. The slide piece 400 mounts onto the tensioner and slides longitudinally in a distal to proximal direction on the tensioner, perpendicular to the cut surface of the tibia. The measurer 400 is then advanced proximally until the medial condylar resection paddle 420 abuts against the distal end of the medial condyle. At this point, the transverse bar 414 of the measurer 400 is showing a standard resection level of 10 mm from the distal end of the medial femoral condyle. As indicated in FIG. 1A, the proposed resection cut (B) is parallel to the tibia cut (A).

Figure 3:
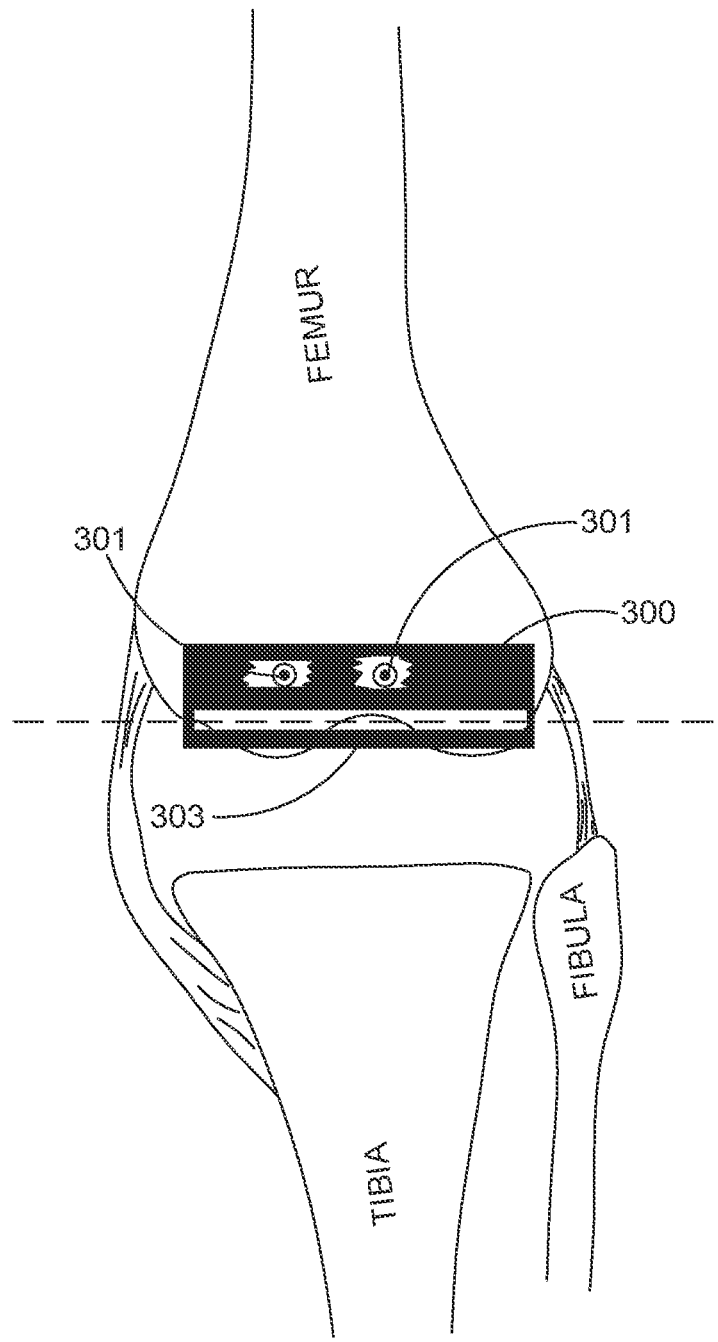
FIG. 3 is a front view of a distal femoral resection guide oriented on guide pins placed using the instrument of FIG. 2.

As shown in FIG. 2, a slide piece pin bore alignment guide 450 is then mounted on the measurer 400. The slide piece alignment guide 450 has "extension" drill holes 451 sized and positioned to match orientation bores 301 on a distal femoral resection guide 300, as indicated in FIG. 3. The slide piece alignment guide 450 is used to accurately position a cutting guide 300 for a distal femoral cut. This ultimately assures that the distal femoral cuts are substantially parallel to the tibial cut. Guide pins are placed through the holes 451 in the transverse arm of the slide piece alignment guide 450 of the measured resection device 400.

As indicated in FIG. 3, the slide piece alignment guide 450 is removed from the distal femoral resection measurer 400. The tensioner 100 and the distal femoral resection measurer 400 are removed from the joint space. With the knee in about 110 degrees of flexion, a distal femoral cutting guide 300 is then positioned on the femur using the guide pins previously placed in the distal femur. The distal cut is made through a resection slot 303 of the cutting guide 300 in a conventional manner. This transfer of position from the slide piece alignment guide 450 positions the cutting guide 300 so that the distal femoral cut is always parallel to the tibial surface. This ensures that the distal medial condyle resection will always be a measured resection corresponding to the exact thickness of the anticipated femoral implant, such as a standard 10 mm distal resection. The lateral condylar distal cut will be a "floating" resection level of variable thickness, but this will always ensure a substantially rectangular extension gap relative to the tibial surface. The key concept is that the distal femoral cut is always linked to the tibial cut through the MCL tension and the tensioner 100. This places the eventual implant where the soft tissue structures of the knee want it to be for ideal kinematic function.

As indicated in FIG. 3, the resulting extension gap should be rectangular, with no need to do soft tissue balancing. The extension gap can be checked with blocks. The technique places the femoral component in a functional position relative to the tibial surface. Ligament isometry causes the femoral component to be where it naturally wants to be, rather than in an arbitrary position based on preselected settings (i.e. 6 degree valgus on an IM guide rod) that may not match the patient's anatomic and mechanical axis. The objective is to achieve natural alignment, which may sometimes be constitutional varus (natural bow-leggedness).

An extra medullary alignment rod can be built into either the resection level measurer (pre-resection) or built into the extension gap blocks (post-resection) for use in assessing the mechanical alignment axis. A C-arm can optionally be used to confirm hip joint center for a very accurate mechanical axis check.

As shown in FIG. 4, after the distal resection, the knee is placed in 90 degrees of flexion. The MCL guided tensioner 100 is inserted into the flexion gap. The tensioner 100 is again stabilized against the tibial bone resection surface by the tibial base plate 110 and the tensioner spike or screw 190 against the roof of the intercondylar notch of the femur. An adaptor may be provided for securing the tensioner 100 to the femoral screw 190 in flexion. The adaptor may include a concave shaped capture device that effectively lifts the screw 190.

The tensioner is then distracted as was done with the knee in extension for the extension gap preparation. The slide piece/resection measuring device 400 is then mounted onto the tensioner 100 and advanced in an anterior direction relative to the femur, and a proximal direction relative to the tibia (knee is in 90 degrees flexion) until the medial condyle foot plate 420 of the resection measurer 400 abuts the posterior medial condyle. The tensioner 100 will naturally set the femoral rotation, and the "flexion" holes in the resection measuring device will be parallel to the tibial cut surface.

Figure 4B:
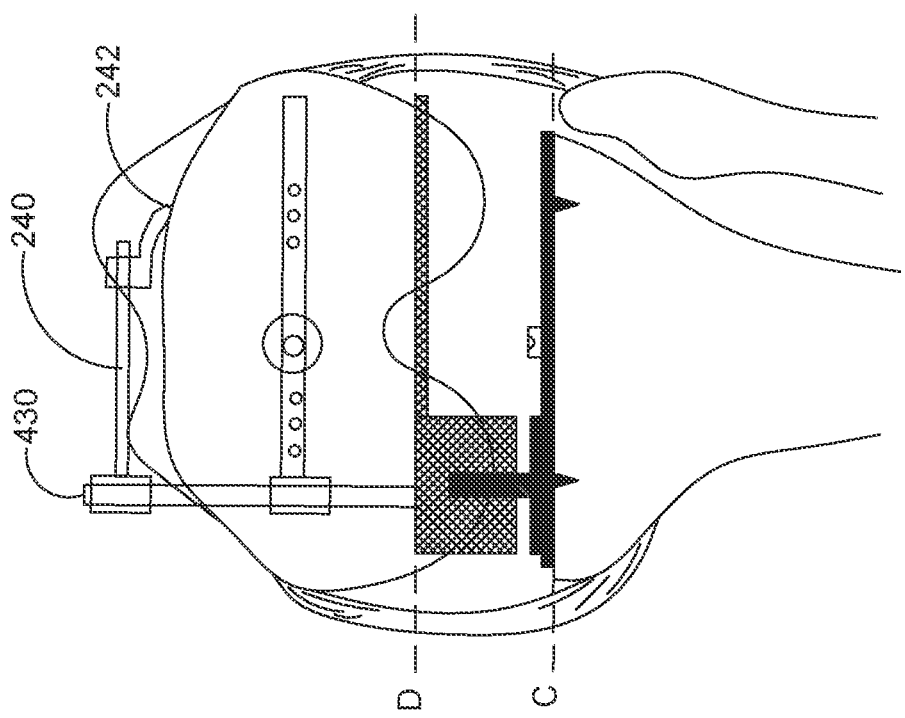
FIG. 4B is front view of one embodiment of a tensioner assembly on a knee in flexion.

As indicated in FIG. 4B, holes are drilled in the distal femoral surface of both condyles through "flexion" holes of the slide piece alignment guide 450. These holes are sized and positioned to match the foot pegs or pin bores of a 4-in-1 posterior referencing distal femoral cutting block. In a standard embodiment, the slide piece/flexion resection measurer 400 sets a measured resection level off of the posterior medial condyle, so as to substantially match the thickness of the femoral implant, such as a 10 to 12 mm resection. As in extension, the lateral condylar posterior resection is variable, as rotation of the femoral resection line will be dictated by ligament tension. The amount of lateral condylar resection is generally less to much less (skim cut) than the medial side. However, due to ligament tensioning, femoral rotation will always be correct. As indicated in FIG. 4B, the posterior condylar resection (line D) will be parallel to the tibial resection (line C), for a resultant rectangular flexion gap. Thus, the tensioner 100 has again linked the tibial and femoral cut surfaces together, and setting of femoral rotation based on ligament tensioning helps prevent flexion instability in the knee implant.

Figure 4A:
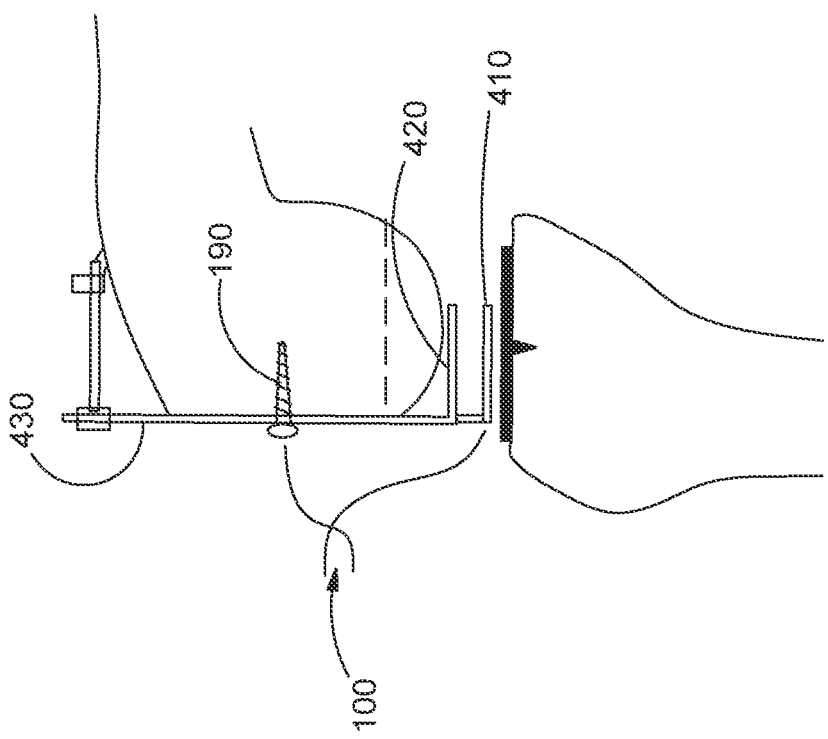
FIG. 4A is a side view of one embodiment of a tensioner assembly on a knee in flexion.

As shown in FIGS. 4A-4B, the resection measuring device 400 can be configured with an anterior post 430 which extends anterior to the medial femoral condyle. In the embodiment of FIG. 4A-4B, the sizing measurement is taken from the posterior medial condyle to the anterior lateral condylar ridge/anterior cortex. A perpendicular stylus arm 240 rotates/swings off of the post 430. A stylette 242 at the end of the arm is configured for use in referencing the lateral condylar ridge (typically the high point anteriorly on a femur) as an anti-notching feature. The level of the perpendicular arm 240 sitting on the post 430 is also a sizing guide to select the proper implant size, as this provides the best measurement of the AP dimension of the femur. The high point of the lateral condylar ridge acts as the anterior reference point, and the line of the resection of the posterior medial condyle is the posterior reference point.

As indicated in FIGS. 4A-B, once the sizing of the implant is determined by the arm 240 and stylette 242, a drill guide is used to set the position of pins for a 4-in-1 cutting block. In some embodiments, calibration lines of the vertical post 430 dictate placement of the drill guide in the A-P orientation. In some embodiments, the instruments may be configured such that the position of the holes is dependent on sizing, such as in a central peg implant system. In other embodiments, the instruments are configured such that the position of the holes remains constant across implant sizes. Size specific holes are drilled for the 4-in-1 cutting block.

The 4-in-1 cutting block is attached to the femur and resections are made in the conventional manner. Trialing is carried out in the conventional manner. The flexion and extension gaps on the trial components should be closely matched. Femoral distal medial and femoral posterior medial cuts are both measured resections (for example, 10 and 11 mm respectively) and are replaced by an equal amount of metallic implant.

Figure 5:
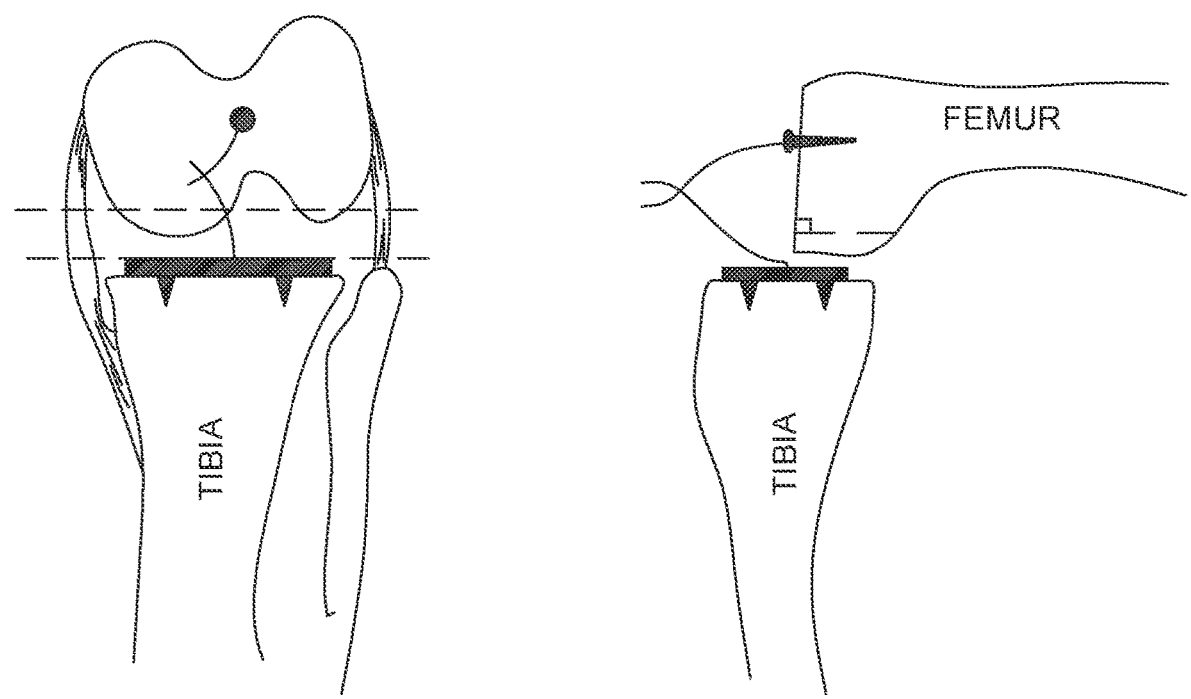
FIG. 5 shows a front and a side view of one embodiment of a tensioner assembly on a knee in flexion.
Figure 6:
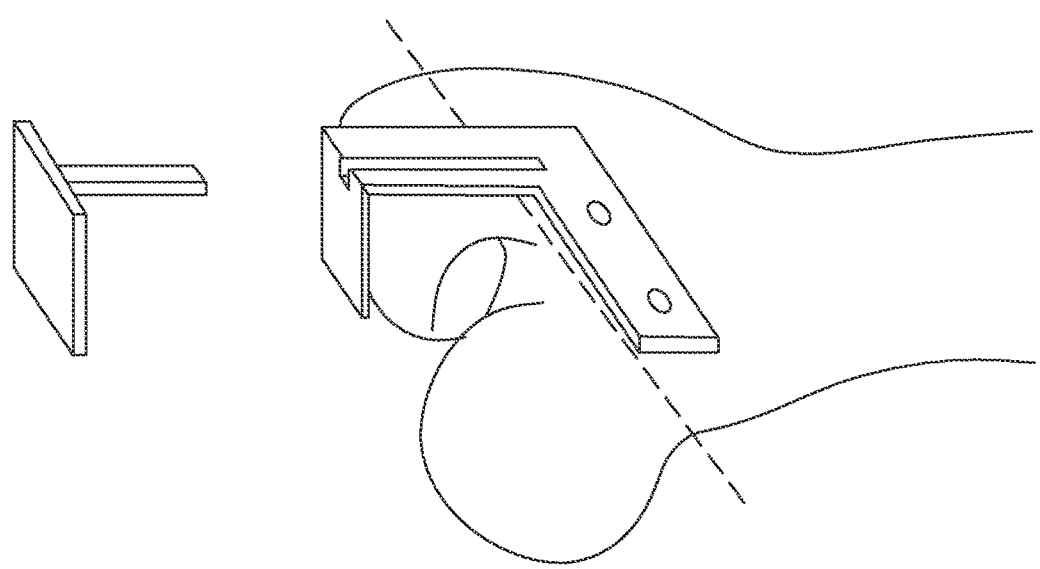
FIG. 6 is a side perspective exploded view of one embodiment of a distal femoral resection measurer configured for use with the tensioner assembly.

FIG. 5 shows a front and a side view of one embodiment of a tensioner assembly on a knee in flexion. FIG. 6 is a side perspective exploded view of one embodiment of a distal femoral resection measurer configured for use with the tensioner assembly.

FIGS. 7-14 show details of one alternative embodiment of instruments and techniques of the invention. FIGS. 7A-7G show steps for using the tensioner assembly 100 to set a distal femoral resection with the knee in extension. FIGS. 8A-8C show steps for using the tensioner assembly 100 to set 4-in-1 femoral resection cuts with the knee in flexion. FIGS. 9-14 show details of the instruments used in the steps shown in FIGS. 7-8.

Figure 12:
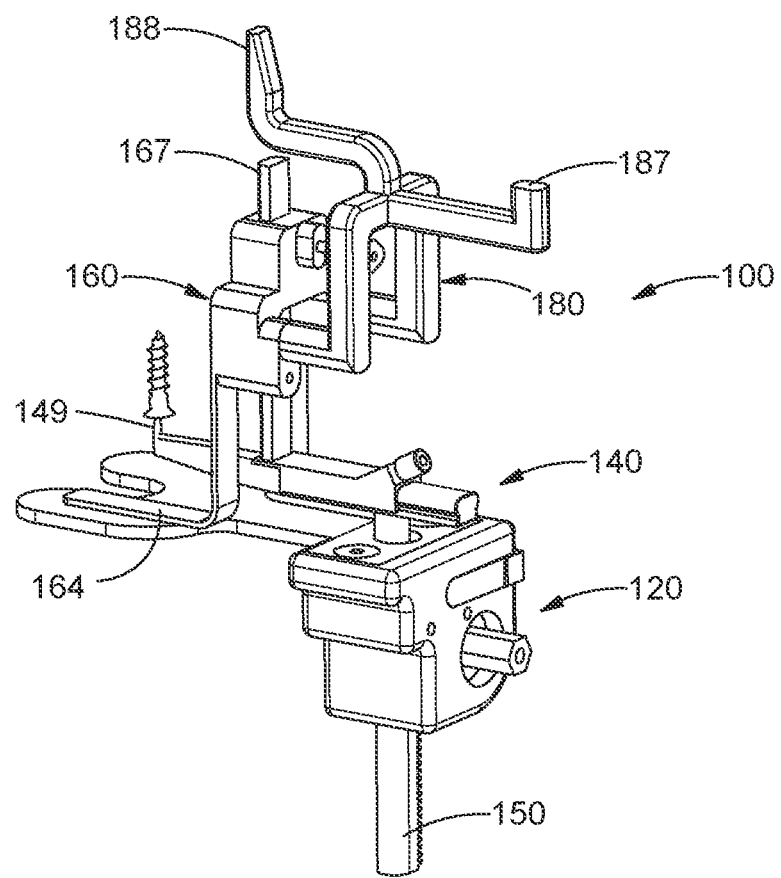
FIG. 12 is a side perspective view of one embodiment of a tensioner assembly.

FIG. 12 shows a tensioner assembly 100 configured for use in extension or flexion. The tensioner assembly 100 comprises, generally, a tensioner body 120, an expander arm 140, a resection arm assembly 160, and an extension angle guide 180 configured for use in setting a distal femoral resection. The embodiment shown in FIG. 12 is for a left knee. The resection arm assembly 160 and the extension angle guide 180 are provided in side specific right and left embodiments. Details of embodiments of the foregoing components will now be described.

Figure 9A:
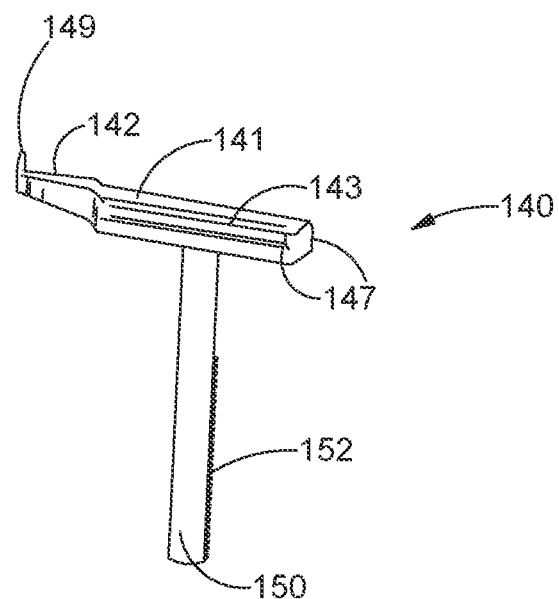
FIG. 9A is a side perspective view of one embodiment of an expander arm for a tensioner assembly.
Figure 9B:
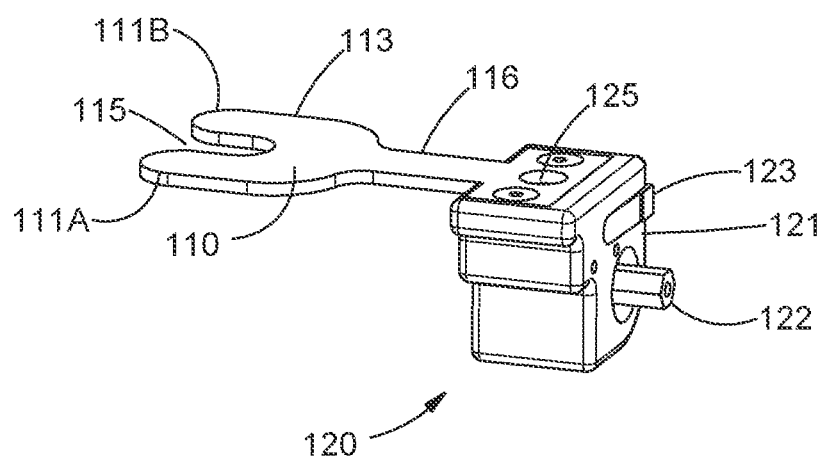
FIG. 9B is a side perspective view of one embodiment of a tensioner body for a tensioner assembly.

FIG. 9B shows details of the tensioner body 120. The tensioner body 120 is configured for placement on a resected proximal tibia. The tensioner body 120 includes a tensioner portion 121 affixed to a substantially planar tibial baseplate 110 via an extension portion 116. In the embodiment of FIG. 9B, the tibial baseplate 110 is attached to the tensioner portion 121 by screws for ease of detachment, but alternative interconnections can be used. The baseplate 110 is generally configured to match the size and shape of the natural resected proximal tibia. In the embodiment of FIG. 9B, the baseplate 110 has an anterior base portion 113. A first and a second posterior extension 111A, 111B extend posteriorly from the base portion 113, forming a posterior groove 115 therebetween. In the embodiment of FIG. 9B, a tibial side of the tibial baseplate 110 does not have spikes.

Figure 9C:
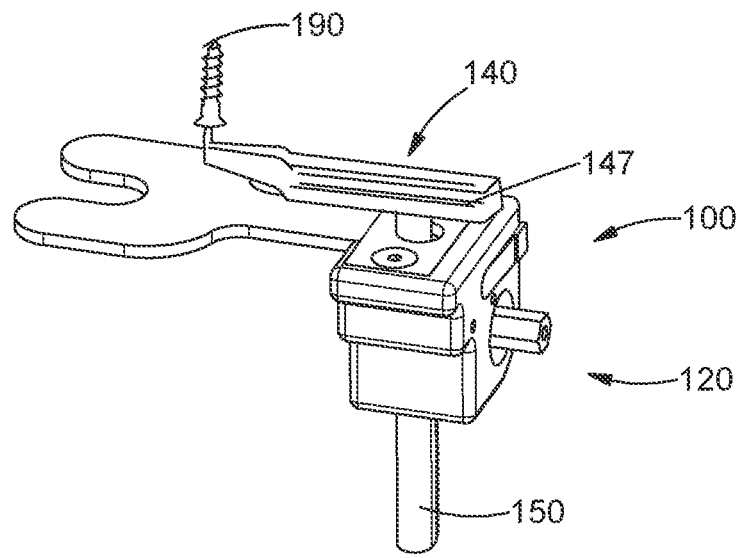
FIG. 9C is a side perspective view of one embodiment of an expander arm on a tensioner body.

The tensioner portion 121 of the tensioner body 120 includes mechanisms for putting the knee in tension. In the embodiment of FIG. 9B, the tensioner portion 121 includes a drive bore 125 extending therethrough. The drive bore 150 is configured to receive a spike arm gear rack post 150 of the expander arm 140, as shown in FIG. 9C. An external drive 122 provides a means for adjusting an internal drive mechanism (not shown). The external drive mechanism 122 is selectively operable by the surgeon to engage the internal drive mechanism, such as with a hex driver. The internal drive mechanism can be configured in various ways, provided the drive mechanism engages and selectively raises and lowers the expander arm 140 via the spike arm gear rack post 150. An external release button 123 is configured to selectively disengage the drive mechanism from the post 150 to thereby release tension in the tensioner assembly 100, such as for removal of the tensioner assembly 100 from the joint, as well as for removing the expander arm 140 from the tensioner body 120.

FIG. 9A shows one embodiment of an expander arm 140 configured for placement on a proximal side of the tibial plate 110. The expander arm 140 includes an elongated body portion 141 and a downwardly depending gear tack post 150. The spiked arm gear rack post 150 extends distally from the expander arm 140 in a substantially perpendicular orientation. A planar distal side of the body portion 141 is configured to rest on the tibial baseplate 110 prior to applying tension via the tensioner body 120. A spiked tip 149 is formed adjacent an anterior end of the expander arm body portion 141. As indicated in FIG. 12, the spiked tip 149 is configured for insertion into the drive socket of the head of the screw 190. Alternatively, the spiked tip 149 can be used directly on the bone without the screw 190, assuming good bone quality. The post 150 is positioned anteriorly a sufficient distance to allow the spiked tip 149 to engage the screw 190 or bone. The expander arm body portion 141 has a pair of longitudinal grooves 147 formed on opposing sides thereof. The longitudinal grooves are sized and configured for engaging a slide piece 160, as described below and shown in FIG. 12.

Figure 10:
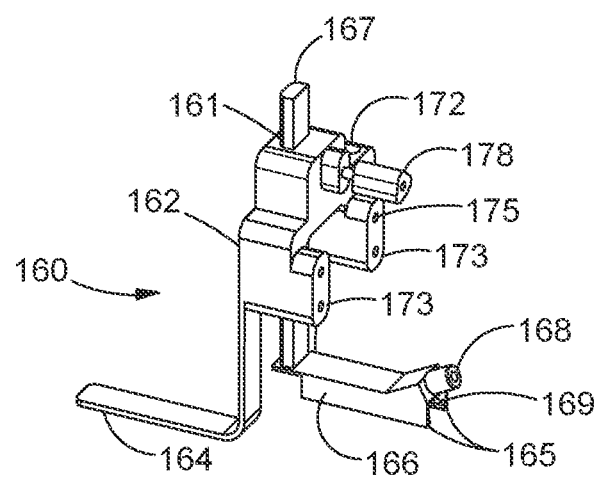
FIG. 10 is a side perspective view of one embodiment of a resection arm assembly.

FIG. 10 shows one embodiment of a slide piece (aka resection arm assembly) 160. The slide piece 160 includes a main body portion 162 slidingly mounted on an attachment base 166 via a post 167. In the embodiment of FIG. 10, the main body portion 162 is unibody structure having a cross piece and a pair of downwardly depending arms. The cross piece has a through bore 161 for slidingly engaging the post 167 of the attachment base. The main body portion 162 slides up and down on the post 167; when a desired position is obtained, the main body knob 178 is used to lock the position of the main body portion 162 on the attachment base 166. The attachment base 166 includes a lengthwise channel 169 sized and configured to receive the body portion 141 of the expander arm 140 therein. A pair of lengthwise rails 165 are formed along the interior of the channel. The rails 165 are sized and configured to slidingly engage the tracks 147 in the expander arm body portion 141. When a desired position is obtained, an attachment base knob 168 is used to lock the position of the slide piece 160 on the expander arm 140. A medial paddle 164 is integrally formed with the main body portion 162. The medial paddle 164 includes a generally planar upper surface configured for resting against the medial condyle, as will be described below. The main body 162 is provided with a pair of extension bores 173 for use in setting pin placement in extension, and a pair of flexion bores 175 for use in setting pin placement in flexion. The bores 173, 175 may be formed on a trailing extension member 176, which extends from a trailing/back face of each of the downwardly depending arms. The trailing extension member 176 can be sized and configured for use in engaging a stylus 240, as will be described below. For use in a sizing step, the main body portion 162 may be provided with a means for attachment of a stylus, such as a bore 172 or a post.

Figure 11:
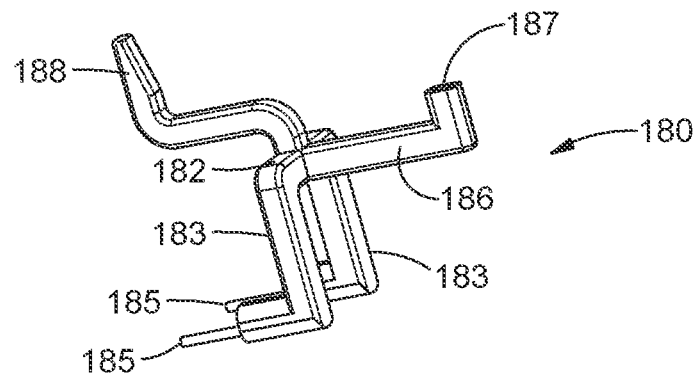
FIG. 11 is a side perspective view of one embodiment of an extension angle guide.

FIG. 11 shows one embodiment of an extension angle guide 180. The extension angle guide 180 includes a main body portion comprising a cross bar 182 having a pair of arms 183 extending downwardly therefrom. A lower end of each arm 183 is provided with a positioning rod 185 on a leading side of the extension angle guide. Each positioning rod 185 is sized and configured to insert into the flexion bores 175 of the main body portion 162 of the slide piece 160, as shown in FIG. 12. As can be seen in FIG. 12, this configuration leaves the extension bores 173 open for use in forming pin bores for a distal femoral resection, as will be described below. A spacer bar 186 extends from a trailing side of the cross bar 182 and terminates in an alignment rod bore 187 positioned for receiving an alignment rod (not shown) for use in verifying alignment in extension. An extension 188 extends from a leading side of the cross bar 182.

FIG. 12 shows a tensioner device 100 configured for use on a knee in extension. The extension assembly of the tensioner device 100 includes the tensioner body 120, the expander arm 140, the resection body assembly 160, and the screw 190. Alternatively, the spiked tip 149 can be used directly against the bone, assuming good bone quality.

Figure 14A:
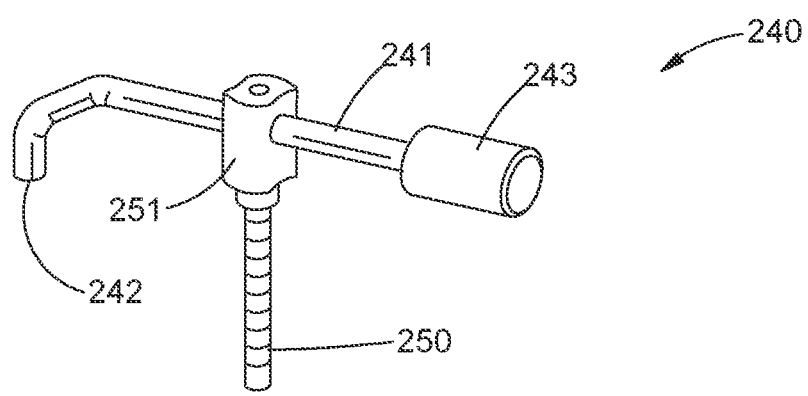
FIG. 14A is side perspective view of one embodiment of a top loading stylus for use with a resection arm assembly.
Figure 14B:
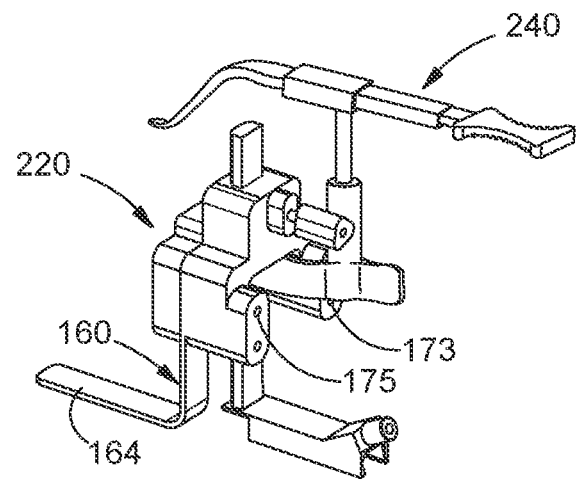
FIG. 14B is a front side perspective view of one embodiment of a front/distal loading stylus on a resection are assembly.

FIG. 14B shows a tensioner device 100 configured for use on a knee in flexion. The flexion assembly of the tensioner device 100 includes the tensioner body 120, the expander arm 140, the resection body assembly 160, and can include a screw 190. Alternatively, the spiked tip 149 can be used directly against the bone, assuming good bone quality. The extension angle guide 180 has been removed. A femoral stylus 240 has been inserted into a proximal stylus bore 172 of the resection body assembly 160 for use in a sizing step. A flexion spacer 220 is attached to a posterior side of the resection body assembly 160.

Figure 13:
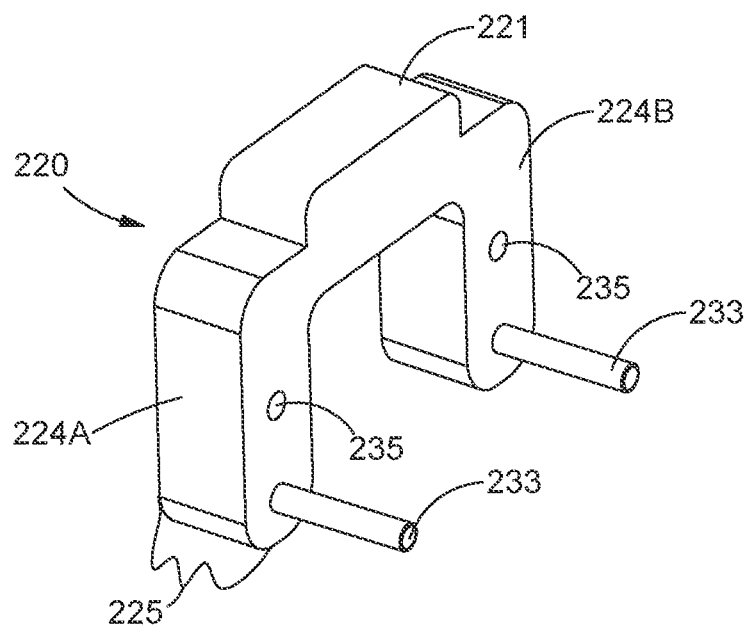
FIG. 13 is a side perspective view of one embodiment of a flexion spacer for use with the tensioner assembly.

FIG. 13 provides details of the flexion spacer 220. The flexion spacer 220 includes a cross bar portion 221 and a pair of arms 224 depending downwardly from the cross bar portion 221. The flexion spacer 220 is configured for selective attachment to the bone contacting/leading side of the main body portion 162 of the slide piece 160. In the embodiment of FIG. 13, this is accomplished by providing a positioning rod 233 extending from a back/trailing face of lower end of each of the downwardly depending arms 224. The positioning rods 233 are sized and positioned to closely fit in the extension bores 173 of the main body portion 162 of the slide piece 160. This configuration leaves the flexion bores 175 open for use in positioning pin bores, while preventing inadvertent use of the extension bores 173.

The flexion spacer 220 has a spacer width 225 between the front/leading and back/trailing faces of the spacer 220. The spacer width 225 can be set to match the depth of the distal femoral resection, or additional thicknesses can be used as needed (such as 10 mm and 15 mm). The spacer width 225 is selected to fill the space between the leading side of the main body portion 162 of the slide piece 160 and the condylar surface, such that the flexion spacer 225 serves as a void filler. The position of the screw 190 or spiked tip 149 in the intercondylar notch determines the M-L position of the slide piece 160. The medial paddle 164 is positioned on the posterior condyle so that it is not too proximal or distal. The medial paddle 164 is fixed at a right angle to the leading face of the main body portion 162 of the slide piece 160. The proper orientation of the spike 190/spiked tip 149 in the intercondylar notch and of the medial paddle 164 on the posterior condyle creates a natural space between the leading face of the main body portion 162 of the slide piece 160 and the resected distal condyle, which is filled with the flexion spacer 220.

Figure 14C:
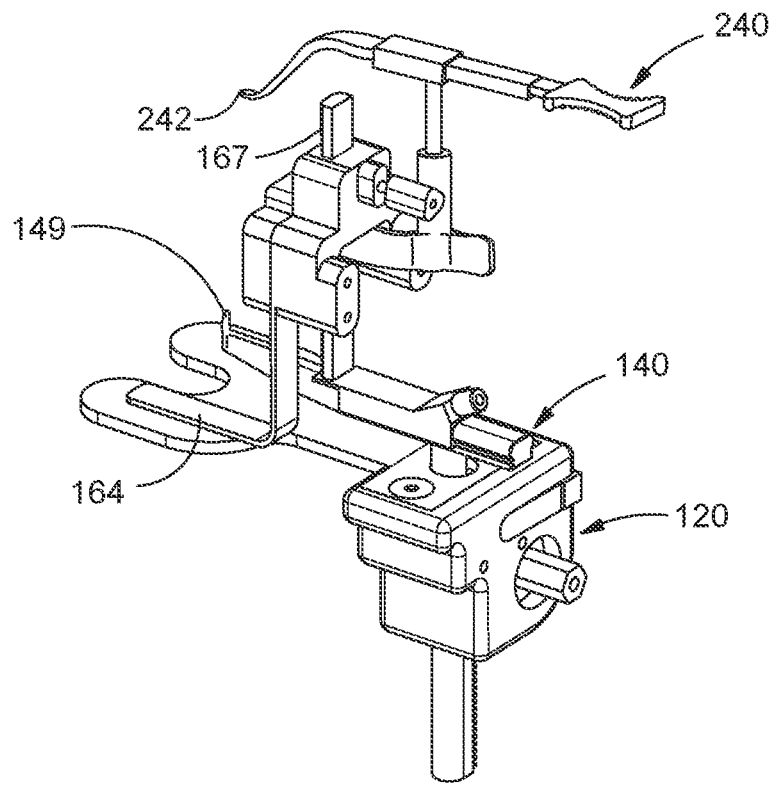
FIG. 14C is a front side perspective view of one embodiment of tensioner assembly including a front/distal loading stylus on a resection are assembly

FIGS. 14A-14C provide details of an assembly of the stylus 240 and the resection arm assembly 160. The stylus 240 can take various forms generally known in the art. In the embodiment of FIGS. 14B-14B, the stylus 240 is a front/distal loading stylus. The stylus 240 can also be top loading. The stylus 240 includes a stylus cross bar 241 disposed between a handle 243 on one end and a tip 242 on an opposing end. The stylus cross bar 241 extends through a stylus receiving member 251 in a sliding arrangement. A stylus post 250 depends downward from the stylus receiving member 251. The stylus post 250 is disposed at about a 90 degree angle to the stylus cross bar 241 and is sized and configured for insertion into the stylus bore 172 on the main body portion 162 of the slide piece 160. The cross bar 241 and post 250 can have size marking indicators thereon, in a manner known to those of skill in the art. While the foregoing features of styluses are generally known in the art, the combination of the stylus 240 with the slide piece 160 and the overall tensioning assembly 100 is unique.

Figure 8A:
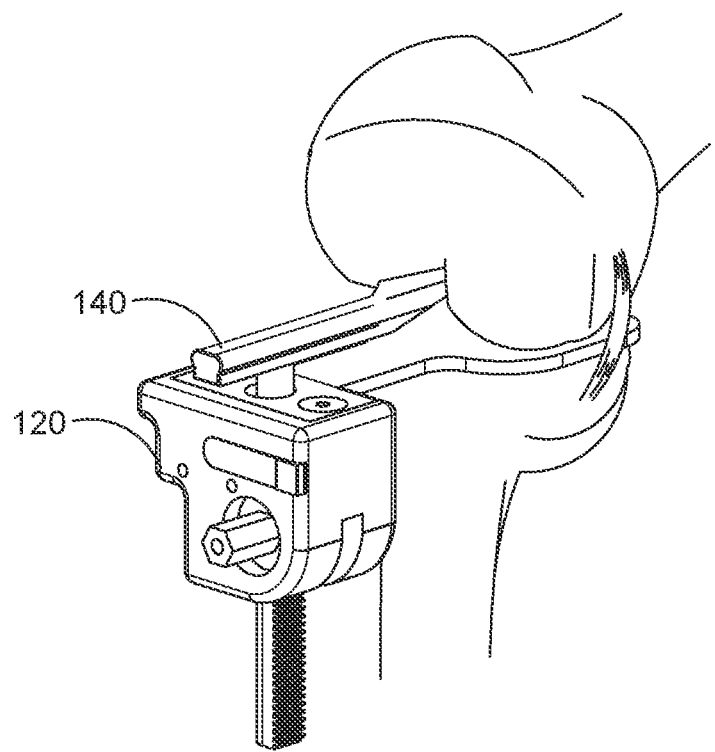
FIG. 8A is front side view of initial placement of a tensioner assembly in a knee in flexion.
Figure 8B:
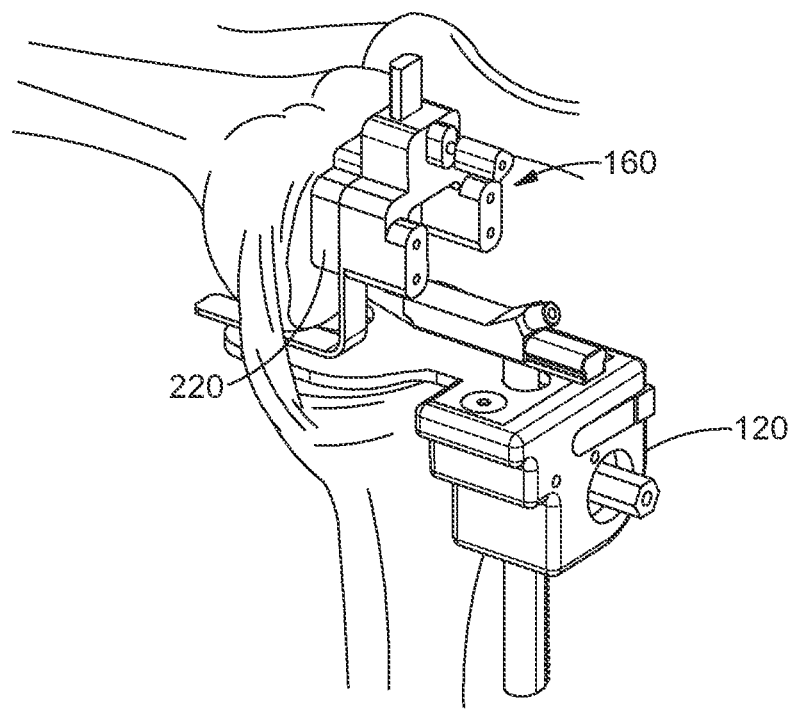
FIG. 8B is a front side view of a tensioner assembly in a knee in flexion, including one embodiment of a slide piece/resection arm assembly 160
Figure 8C:
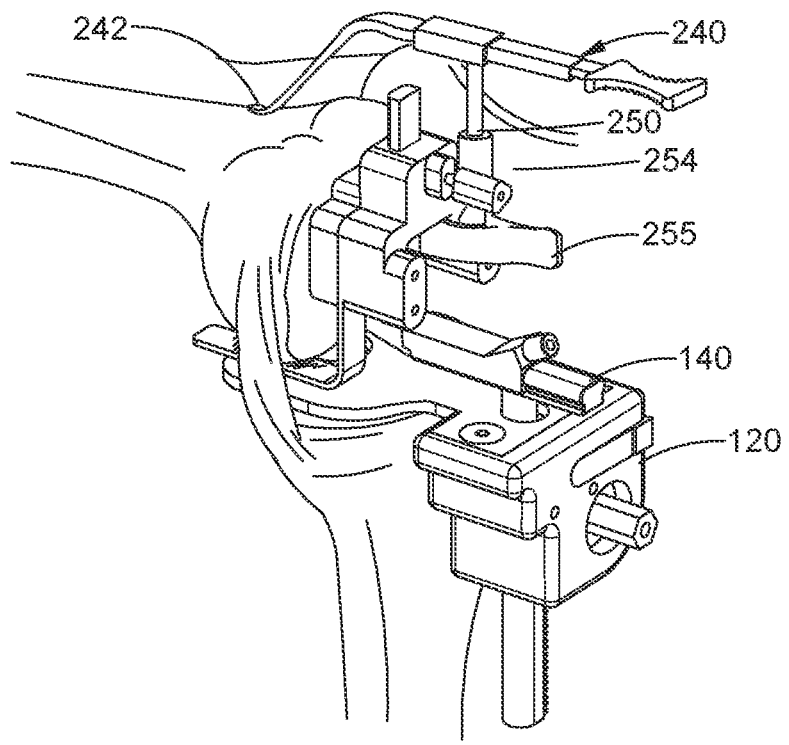
FIG. 8C is a front side view of one embodiment of a tensioner assembly in a knee in flexion, including a removable stylus.
Figure 15A:
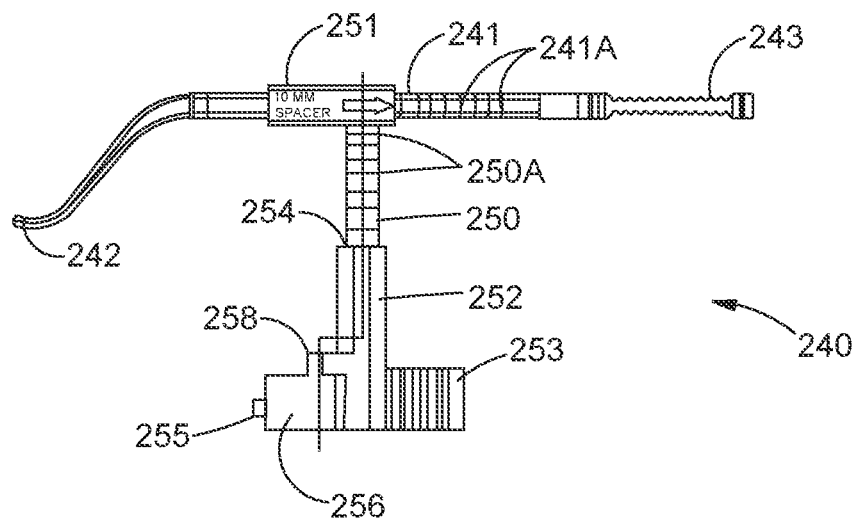
FIG. 15A is side view of one embodiment of a front/distal loading stylus for use with a tensioner assembly.
Figure 15B:
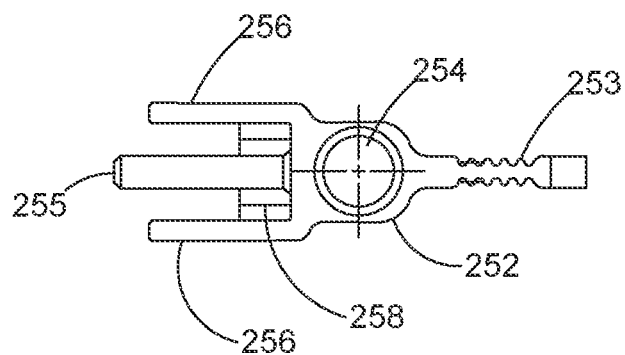
FIG. 15B is bottom view of the stylus of FIG. 15A.

FIGS. 15A and 15B show an embodiment of a front/distal loading stylus 240. The front/distal loading stylus 240 readily slides into the trailing face of the main body portion 162 of the slide piece 160. FIGS. 8C and 14C show the front/distal loading stylus 240 on a slide piece 160 in a tensioning assembly 100. The front/distal loading stylus 240 engages and disengages the slide piece 160 more easily than a top loading stylus when working in the confines of the knee joint. In the embodiment of FIGS. 15A-B, a lower portion of the stylus post 250 is slidingly engaged to an upper portion of the attachment member body 252, such as via a bore 254. The cross bar 241 and post 250 may be provided with size indicator marks 241A, 250A, in a manner known to those of skill in the art. The attachment member body 252 is configured to selectively attach to the back/trailing face of the slide piece 160. The attachment member body 252 includes an engagement feature that is configured to selectively fit into a matching engagement feature on the main body portion 162 of the slide piece 160. In the embodiment of FIGS. 15A-B, the engagement feature includes a peg 255 sized and positioned to fit in one of the flexion bores 175, a pair of opposing side walls 256 configured to closely sandwich the trailing extension 176, and an upper ledge 258 positioned and configured to closely envelop an arched upper end of the trailing extension 176, as shown in FIG. 8C. The combination of these structures allows the stylus 240 to readily and firmly engage the slide piece 160 without comprising the multipurpose use of the main body portion 162 for the various other functions described herein. The engagement member 254 may be provided with a handle 253 for use in inserting and removing the stylus 240 from the slide piece 160.

Methods of use of the foregoing instruments will now be described with reference to FIGS. 7-8. Exposure to the knee joint is gained through a typical surgical incision for TKA. The tibia is subluxated. The fat pad and menisci are excised. The cruciate ligaments are detached from the femur. Any significant osteophytes are removed from the femur and tibia.

The technique can be based on a "non-anatomical" zero degree varus/valgus cut of the proximal tibia in the coronal plane, perpendicular to the mechanical long axis of the leg. However, the cut does not have to be zero degrees; the femoral cuts will always be linked to the tibia at whatever varus/valgus angle the tibia is resected. It is critical to get a good tibial cut, since subsequent cuts are based on the tibial cut. Use of extra-medullary alignment guides is recommended for accuracy. Placement should be center to just medial of center on the tibial plateau, and center of the ankle mortise. Portable X-ray can be used for additional accuracy, but may not be practical.

The amount of tibial slope is at the surgeon's preference. In general, 0 degrees, 3 degrees, or matching the patient's posterior tibial slope is suggested. The tibial resection depth is at the discretion of the surgeon. As long as resection is adequate, the exact amount is inconsequential, as extension and flexion gaps are affected equally.

If bone quality is poor, a screw 190 can be used as the spike 190. A pilot hole for the screw 190 is created in the distal femoral canal, such as with a ⅛" diameter drill bit. The hole may be placed medial and anterior to the anteromedial corner of the intercondylar notch, in the center of the trochlear groove, or 1 cm (0.4") anterior to the PCL origin. A screw 190, such as a 25 mm×6.5 mm knee bone screw, is driven into the pilot hole until the head of the screw 190 is flush with the surface of the cartilage. The length of the screw 190 is preferably too short to enter the femoral IM canal, which lowers the risk of fat emboli and reduces blood loss, particularly in comparison to an IM rod.

As will be described in further detail below, if bone quality is good, the screw 190 is not necessary and the spiked tip 149 of the expander arm 140 can positioned directly on the femur. At any point in the procedure, any osteophytes that are limiting placement or movement of instruments are removed.

Figure 7A:
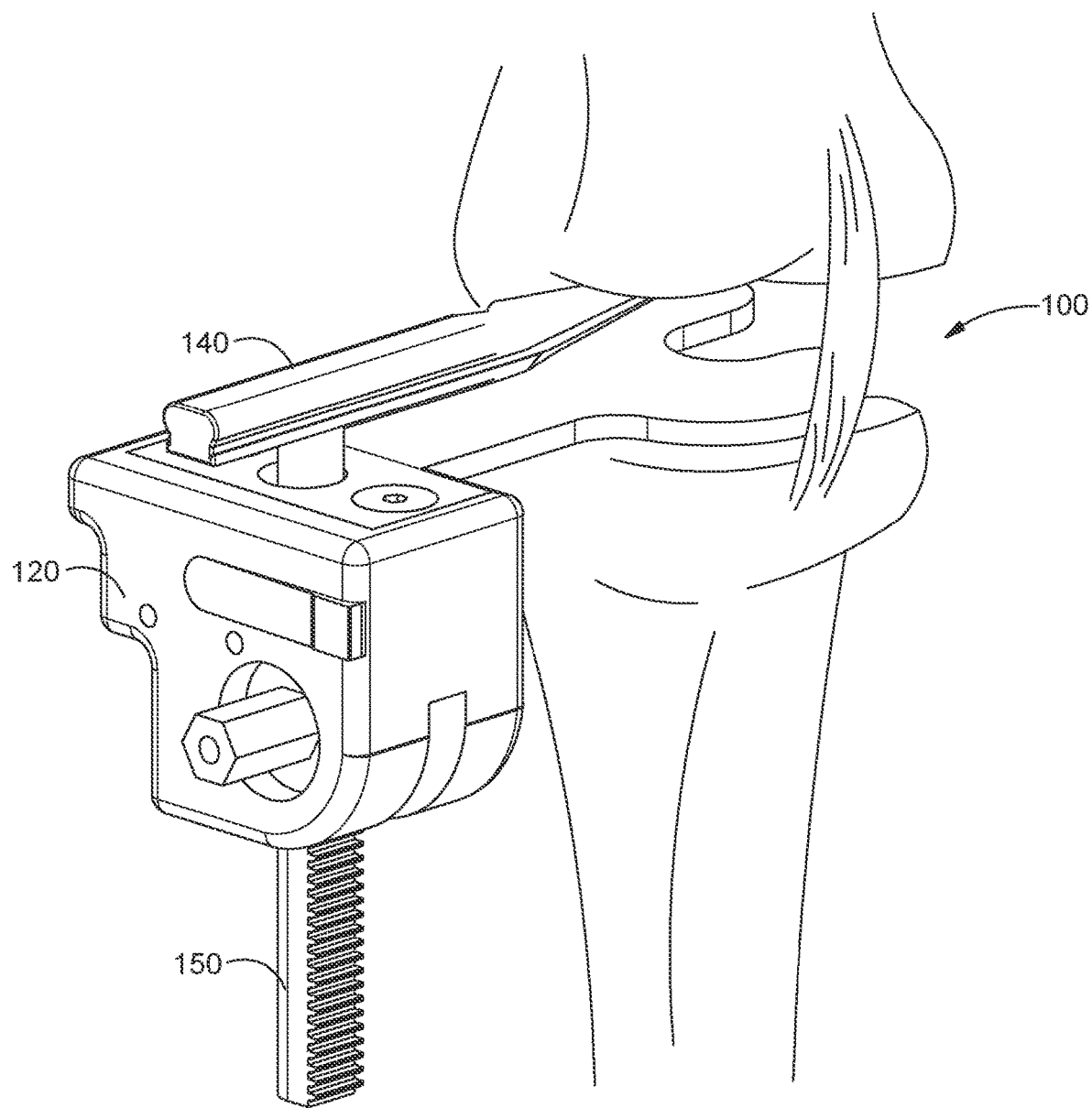
FIG. 7A is side perspective view of one embodiment of a tensioner assembly on a knee in extension.
Figure 7B:
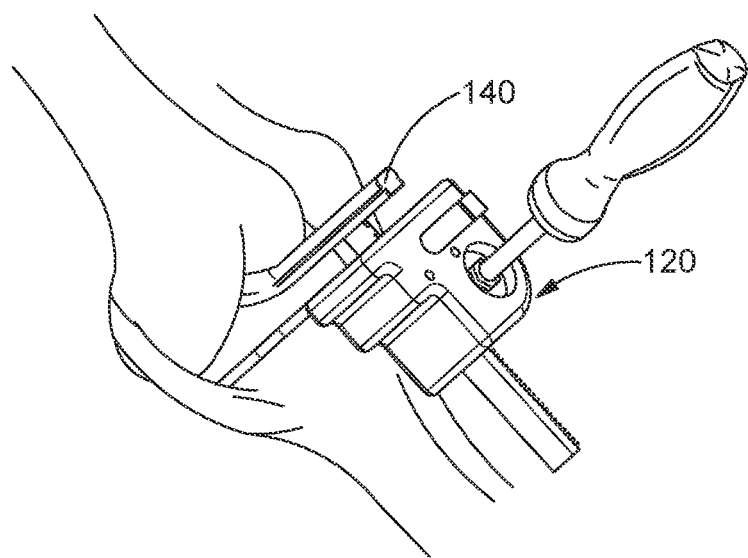
FIG. 7B is a front-side view showing tensioning of a tensioner body of a tensioner assembly with a torque limiting driver.
Figure 7C:
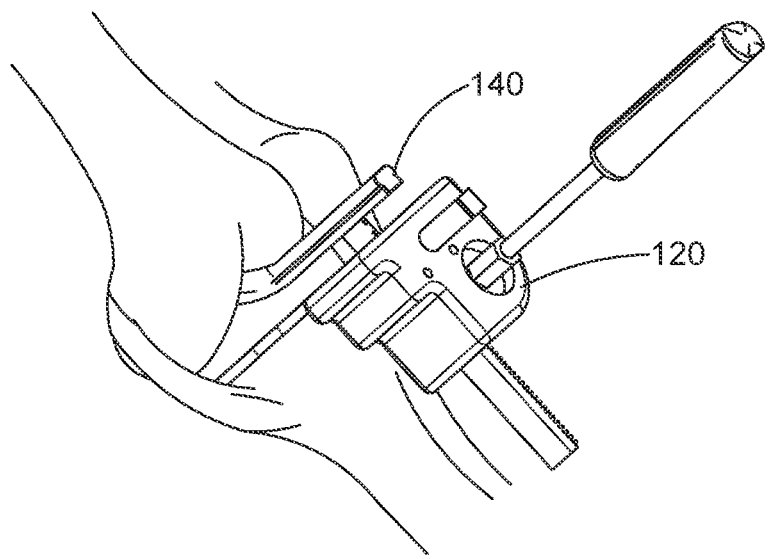
FIG. 7C is a front-side view showing tensioning of a tensioner body of a tensioner assembly with a screwdriver.

The initial steps are carried out with the joint in extension. The expander arm 140 is inserted into the bore of the tensioner body 120. As shown in FIG. 7A, the expander arm 140 is inserted into the joint space such that the tibial plate 110 of the tensioner body 120 rests on the resected tibial plateau. If a screw 190 is used, the spiked tip 149 of the expander arm 140 is inserted into the driving socket of the screw 190. As shown in FIGS. 7B and 7C, a screwdriver, such as a torque limiting driver (FIG. 7B) or a hex driver (FIG. 7C), is used to engage and turn the external drive 122 of the tensioner body 120 in order to raise the spike arm gear rack post 150 relative to the tensioner body 120. This action expands the expander arm 140 relative to the tibial plate 110, which applies tension to the collateral ligaments. The tensioner body 120 and expander arm 140 are adjusted (expanded) until the proper ligament tension is achieved.

Figure 7D:
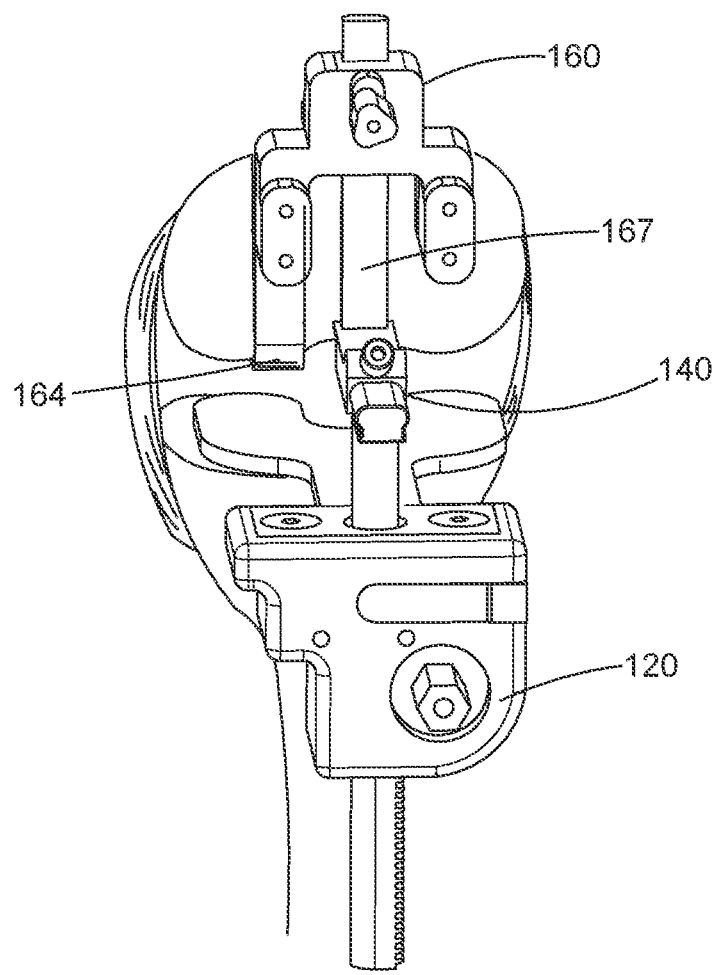
FIG. 7D is a front view of a tensioner assembly with a slide piece/resection arm assembly connected to the expander arm.

As indicated in FIG. 7D, with the ligaments under tension, the slide piece/resection arm assembly 160 is inserted into the joint space and connected to the expander arm 140 in a sliding relationship. In the embodiment of FIG. 7D, the attachment base 166 of the slide piece/resection arm assembly 160 slides onto the expander arm body portion 141 of the expander arm 140. The slide piece 160 is slid toward the condylar resection surface until the main body portion 162 of the slide piece 160 contacts the bone surface. The main body portion 162 is then slid upward/proximally along the post 167 until the medial paddle 164 contacts the distal medial condyle.

Figure 7E:
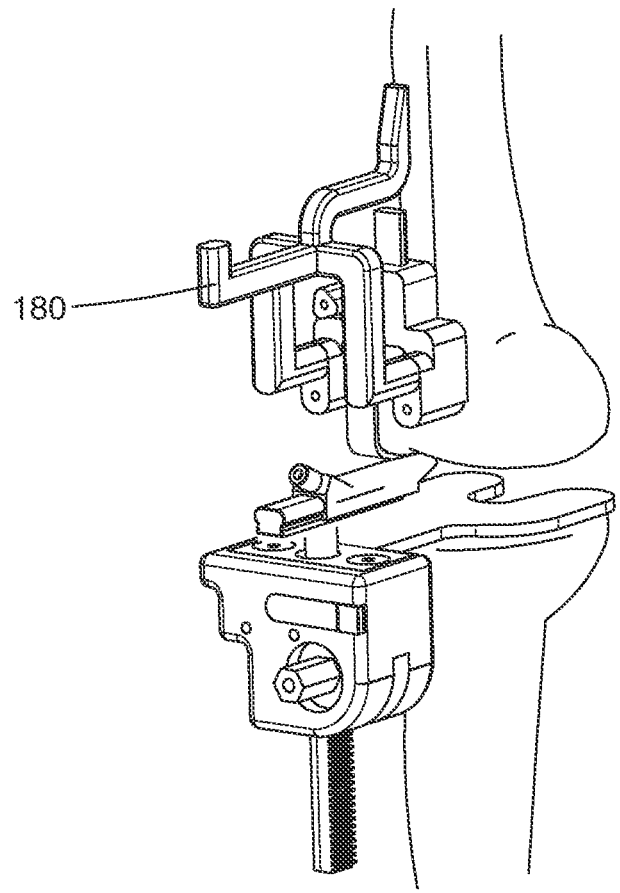
FIG. 7E is front side perspective view of use of one embodiment of an extension angle guide on the tensioner assembly.
Figure 7F:
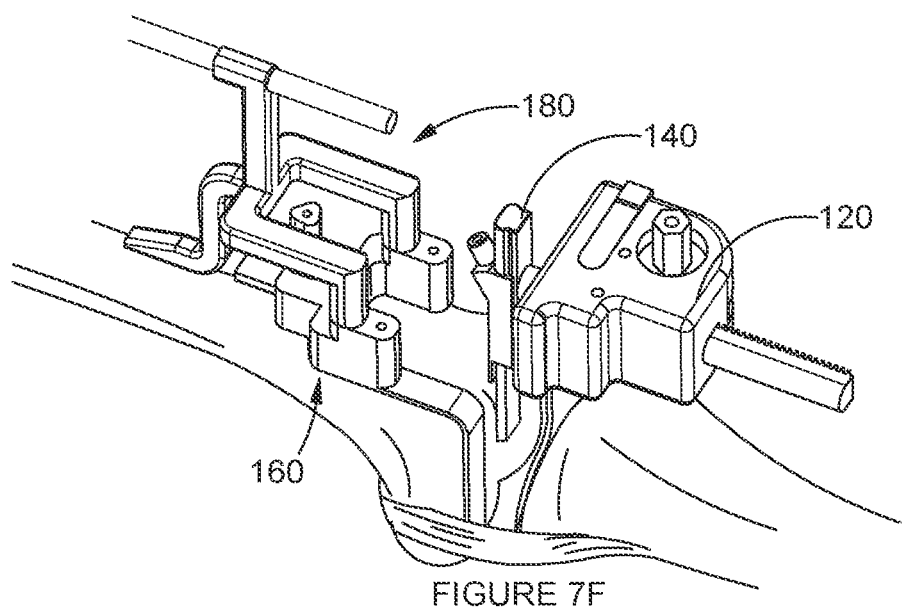
FIG. 7F is side perspective view of use of an alignment rod in one embodiment of an extension angle guide on the tensioner assembly to confirm extension alignment.

As indicated in FIG. 7E, the extension angle guide 180 is attached to the slide piece/resection arm assembly 160. As indicated in FIG. 7F, extension alignment is confirmed by placing an alignment rod in the alignment rod bore 185 of the extension angle guide 180. Once everything is positioned, the resection arm assembly 160 is locked into position on the expander arm 140. With the medial paddle 164 contacting the distal medial condyle, the main body knob 178 is used to lock the position of the main body portion 162 on the post 167 of the attachment base 166. The attachment base knob 168 is used to lock the attachment base 166 to the expander arm body portion 141.

As can be appreciated from the foregoing, the setting of tension in the ligaments and the setting of the position of the drill guide are independent steps that are decoupled from one another. First, tension is set using the expander 140. After tension is set, the position of the drill guide is aligned by adjusting and locking the position of the slide piece 160, as described above.

Guide holes are formed in the distal femur by drilling through the extension bores or guide holes 173 of the resection arm assembly 160. The extension guide holes 173 may be marked (e.g. "EXT") to indicate that they are for use in extension. Smooth pins are inserted into the holes.

Because the knee joint is under tension and the tensioner assembly 100 is attached to the intracondylar notch via screw 190 or spiked tip 149, removal of the tensioner assembly 100 is accomplished by releasing tension and disassembling the tensioner assembly 100. The following steps can be used to remove the tensioner assembly 100 from the joint space. First, the resection arm assembly 160 is unlocked from the post 167 and from the expander arm 140. Next, the expander arm 140 is released by providing a small amount of additional tension through the driver and then pressing the release button to allow the tensioning device to retract to its compact state. The resection arm assembly 160 is then pulled anteriorly to slide the resection arm assembly 160 off of the expander arm 140 and the pins. The tensioner body 120 can be removed from the joint space by placing the knee in a slight bit of flexion and allowing the expander arm 140 tip to disengage from the screw head. The expander arm 140 tip should be fully removed from the screw head 190 before trying to remove the tensioner body 120 and expander arm 140 from the joint space.

Figure 7G:
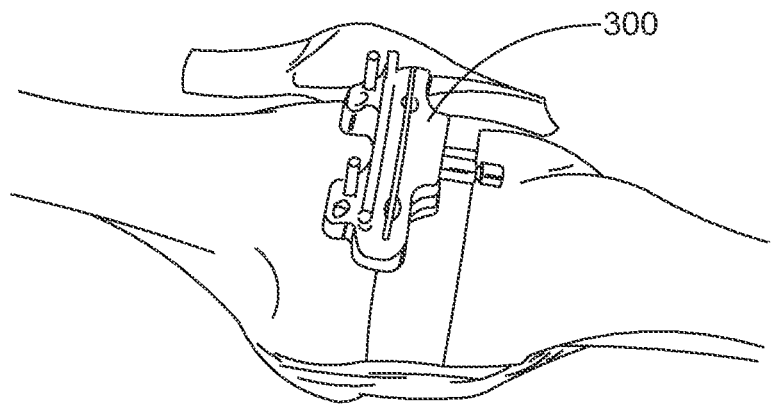
FIG. 7G is a front view of a distal femoral resection guide placed on pins placed using the tensioner assembly.

If a bone screw 190 was used, the bone screw 190 is removed from the femur prior to the distal resection. As shown in FIG. 7G, a distal cut guide 300, such as a 10 mm cut guide, is placed over the previously placed pins such that the pins pass through the holes of the cut guide 300. The knee is placed at about 110 degrees of flexion for the distal resection. The distal cut guide 300 is used to make the distal resection in a manner known to those of skill in the art.

After completion of the distal femoral cut, the knee joint is placed in 90 degrees of flexion. As shown in FIG. 8A, the tensioning device 100 is reintroduced into the joint space. The tibial plate 110 of the tensioner body 120 is placed against the resected surface of the tibia. The tip 149 of the expander arm 140 is placed in the intercondylar notch (alternatively, if a screw 190 was used, the tip 149 may be placed in the screw). The tensioning device 100 is expanded to apply tension to the collateral ligaments. The flexion spacer 220 is attached to the resection arm assembly 160. With the ligaments under tension, the slide piece 160 and attached flexion spacer 220 are attached to the expander arm 140, as described above in the extension steps. The position of the main body portion 162 of the slide piece 160 is adjusted up along the post 167 until the paddle 164 contacts the posterior surface of the medial condyle. The flexion of the knee is adjusted so that the spacer 220 rests flush against the distal femoral resection, which ensures that the device is at 90 degrees to the distal femoral resection.

With the paddle 164 contacting the medial condyle and the spacer 220 contacting the resected distal femur, the resection arm assembly 160 is locked into position via the main body knob 178 and the attachment base knob 168. The resection arm assembly 160 includes two flexion guide holes 175 (typically, ⅛ inch diameter) for use in flexion. The flexion guide holes 175 may be marked (e.g. "FLEX") to indicate that they are for use in flexion. The surgeon drills a drill bit through the flexion guide holes of the resection arm assembly 160.

A femoral sizing method that integrates with the tensioner instruments is shown in FIG. 8C. As shown in FIG. 8C, a sizing stylus 240 is inserted into the resection arm assembly 160. With the paddle 164 of the resection arm assembly 160 contacting the posterior medial condyle, the tip 242 of the sizing stylus 240 is brought into contact with the most prominent aspect of the anterior lateral cortex of the femur. The femoral size is determined by reading the markings on the post 250 of the sizing stylus 240 where the post 250 protrudes from the body of the resection arm assembly 160. The resection arm assembly 160 is then unlocked and removed from the joint space. The expander arm 140 is released by providing a small amount of additional tension and then pressing the release button to allow the tensioning device to retract to its compact state. The tensioning device 100 is removed from the joint space. (Alternatively, sizing can be determined by alternative methods after removal of the tensioner 100).

A series of sizes of 4-in-1 resection blocks are provided, such as in sizes 1 to 8. Each of the resection blocks has posterior referencing pegs that match the spacing of the flexion bores, in a configuration known to those of skill in the art. An appropriately sized 4-in-1 resection block is selected, based on the size determined in the foregoing sizing step. The 4-in-1 block is placed on the femur such that the pegs are in the flexion holes (for small sizes, such as 1 and 2, it may be necessary to use a re-drill guide to shift the location of the holes). The femoral resection block is preferably sized so that it can be used to double-check the width of the femoral implant and the depth of the posterior condyles of the femoral implant. The 4-in-1 block is used to make anterior, posterior, posterior chamfer, and anterior chamfer resections, in a manner known to those of skill in the art. Trial reduction is then carried out using conventional procedures.

The overall result is that the tensioner 100 utilizes the natural length and tension of the MCL and LCL to achieve parallel distal femoral and posterior femoral cuts to the original tibial cut. This essentially links the femoral and tibial cuts together for rectangular extension and flexion gaps, and overall proper kinematic alignment of components in extension and flexion.

The MCL based ligament tensioner 100 is based on the premise that the patient's MCL is normal or near normal in length and strength, and that it should be the guiding structure to determine proper positioning of the TKA components. If bone resections are done properly, the MCL should not need balancing. Conversely, the need for soft tissue balancing is an indicator of failure to achieve proper placement of bone cuts.

Femoral distal lateral and femoral posterior lateral cuts are both tensioned resections (variable based on the tensioner's ability to distract the joint spaces to the point of ligament isometry), and the resulting point of parallelism to the tibial resection surface. These lateral condylar bone resections will vary from one knee to the next based on the effects on bone resection angles provided by the tensioner device.

Occasionally, the knee will remain tight in extension following all bony resections, despite having rectangular gaps. This is due to a tight posterior capsule, which can be resolved with a capsular release. This usually occurs in the setting of a preoperative existing flexion contracture. Additional bone resection (distal femur) is generally not needed.

The instruments can be assembled in the form of a kit. The components of the kit are preferably arranged in a convenient format, such as in a surgical tray or case. However, the kit components do not have to be packaged or delivered together, provided that they are assembled or collected together in the operating room for use at the time of surgery.

As can be appreciated from the foregoing discussions, the instruments and techniques of the invention provide major and unique advantages for TKA, including: no violation of the medullary canal in either the femur or tibia, reducing the risk of fat emboli; the tensioner 100 is used for both the extension and flexion gaps; the tensioner 100 allows soft tissue structures to self-align the femur relative to the tibial resection surface and create parallel femoral (distal and posterior) cuts to the tibial surface, resulting in rectangular extension and flexion gaps; the tibial cut and femoral cuts (distal and posterior) are linked together through the tensioner's 100 unique use of collateral ligaments in both extension and flexion; femoral cuts are determined by and based on the original tibial cut; tensioner 100 results in a consistent measured 10 mm or appropriate amounts of bone resection of the medial femoral condyle in extension (distal cut), and flexion (posterior cut); the lateral condylar bone cuts are variable, or "floating" resections at whatever thickness is necessary to result in a parallel cut surface to the tibial cut surface; the tensioner 100 has a built-in feature to measure the anterior-posterior dimensions of the distal femur, essentially determining the size of the 4-in-1 cutting block; the A-P dimension is from the posterior medial surface of the condyle to the anterior lateral surface of the distal condylar flair, which gives an accurate AP dimension of the distal femur in order to prevent "notching" of the anterior femoral cortex; less pain to the patient because the ligaments are not disturbed as much as they often are with other systems. The concepts of the invention are consistent with a "medial pivot" knee implant philosophy.

In one preferred embodiment, the system is configured as a posterior referencing system in which the system always removes the same amount of bone on the posterior of the femoral condyles. If it is necessary to upsize or downsize the knee implant, the ligament balancing will not be upset, unlike anterior or distal referencing systems. This results in a system that is more stable than anterior or distal referencing systems.

Although the present invention has been described in terms of specific embodiments, it is anticipated that alterations and modifications thereof will no doubt become apparent to those skilled in the art. It is therefore intended that the following claims be interpreted as covering all alterations and modifications that fall within the true spirit and scope of the invention.

What is claimed is:

1. A device for preparing a femur of a patient for receipt of a knee implant in flexion relative to a resected tibia plateau based on applying a tension to medial and lateral collateral ligaments of said patient, comprising:
    a tibial baseplate configured to rest on said resected tibial plateau,
    a tensioner, the tensioner comprising a tensioner body having a tensioner portion, the tensioner portion affixed anteriorly to the tibial baseplate,
    an expander arm comprising an elongated body portion, a superior side of the elongated body portion having a spiked tip adjacent a posterior end thereof, the spiked tip positioned to selectively interact with an intracondylar notch of the knee under tension, the expander arm operatively connected to the tensioner body via the tensioner portion, the tensioner portion configured for use in selectively raising and lowering the expander arm relative to the tibial baseplate to thereby apply the tension to said medial and lateral collateral ligaments of said patient in flexion, and
    a resection arm assembly, the resection arm assembly configured for selective attachment to the expander arm, the resection arm assembly including a main body portion, the main body portion supporting a medial paddle,
    wherein the spiked tip, when interacting with the intercondylar notch and the medial paddle, is sized and configured to maintain a space between a proximal face of the main body portion of the resection arm assembly and a resected distal portion of the medial condyle, and
    further comprising a flexion spacer, the flexion spacer configured to attach to the leading face of the main body portion and sized to fill the space.

2. The device of claim 1, wherein the expander arm is operatively connected to the tensioner portion via a rack post, the rack post having a plurality of ratchet teeth configured to engage the tensioner portion for use in selectively raising or lowering the expander arm relative to the tibial baseplate.

3. The device of claim 2, the tensioner portion having a drive bore extending therethrough, the drive bore operatively receiving the rack post therein.

4. The device of claim 2, wherein the tibial baseplate is substantially planar.

5. The device of claim 4, wherein the tensioner portion is affixed anteriorly to the tibial baseplate via an extension portion of the tibial baseplate.

6. The device of claim 1, wherein the resection arm assembly further comprises an attachment base and the main body portion slidingly mounted on the attachment base via a post, wherein the attachment base is configured to slide onto the expander arm.

7. The device of claim 6, wherein the main body portion is configured to selectively lock the main body portion to the post of the attachment base to thereby maintain a selected position of said resection arm assembly relative to said knee.

8. The device of claim 1, wherein the main body portion has pin bores formed therethrough for use in setting pin placement into the femur, the pin bores positioned to correspond with pin bores on associated resection guides.

9. The device of claim 8, wherein the pin bores include a pair of extension bores for setting pin placement into the femur when in extension and a pair of flexion bores for setting pin placement into the femur when in flexion.

10. The device of claim 6, wherein the attachment base has a lengthwise channel sized and configured to receive the elongated body portion of the expander arm therein.

11. The device of claim 10, wherein the expander arm body portion of the expander arm is provided with a pair of opposing tracks, and the lengthwise channel of the attachment base has a pair of opposing rails, the rails sized and configured to slide into the tracks from an anterior-to-posterior orientation.

12. A device for preparing a femur of a patient for receipt of a knee implant in flexion relative to a resected tibia plateau based on applying a tension to medial and lateral collateral ligaments of said patient, comprising:
    a tibial baseplate configured to rest on said resected tibial plateau, a tensioner, the tensioner comprising a tensioner body having a tensioner portion, the tensioner portion affixed anteriorly to the tibial baseplate, an expander arm comprising an elongated body portion, a superior side of the elongated body portion having a spiked tip adjacent a posterior end thereof, the spiked tip positioned to selectively interact with an intracondylar notch of the knee under tension, the expander arm operatively connected to the tensioner body via the tensioner portion, the tensioner portion configured for use in selectively raising and lowering the expander arm relative to the tibial baseplate to thereby apply the tension to said medial and lateral collateral ligaments of said patient in flexion, and a resection arm assembly, the resection arm assembly configured for selective attachment to the expander arm, the resection arm assembly including a main body portion, the main body portion supporting a medial paddle, wherein the resection arm assembly further comprises an attachment base, the main body portion is slidingly mounted on the attachment base via a post, and the attachment base is configured to slide onto the expander arm, and wherein the attachment base has a lengthwise channel sized and configured to receive the elongated body portion of the expander arm therein.

13. The device of claim 12, wherein the spiked tip, when interacting with the intercondylar notch and the medial paddle, when interacting with a posterior portion of the medial condyle, are sized and configured to maintain a space between a proximal face of the main body portion of the resection arm assembly and a resected distal portion of the medial condyle, and further comprising a flexion spacer, the flexion spacer configured to attach to the leading face of the main body portion and sized to fill the space.

14. The device of claim 12, further comprising an extension angle guide selectively attachable to the resection arm assembly in extension, the extension angle guide configured for use in setting a distal femoral resection.

15. The device of claim 12, further comprising a removable stylus on the main body portion of the resection arm assembly, the stylus configured for use in sizing said femur in flexion.

16. The device of claim 15, wherein the stylus is an anterior loading stylus, for ease of attachment and detachment of the stylus.

17. The device of claim 14, wherein the device is configured for use on either a left or a right knee.

18. The device of claim 12, wherein the expander arm is operatively connected to the tensioner portion via a rack post, the rack post having a plurality of ratchet teeth configured to engage the tensioner portion for use in selectively raising or lowering the expander arm relative to the tibial baseplate.

19. The device of claim 18, the tensioner portion having a drive bore extending therethrough, the drive bore operatively receiving the rack post therein.

20. The device of claim 12 wherein the tensioner portion is affixed anteriorly to the tibial baseplate via an extension portion of the tibial baseplate.

* * * * *